(12) United States Patent
Amanai et al.

(10) Patent No.: US 10,551,617 B2
(45) Date of Patent: Feb. 4, 2020

(54) IMAGE PICKUP APPARATUS WHICH CORRECTS CHROMATIC ABERRATION IN A WIDE WAVELENGTH RANGE, AND CAPSULE ENDOSCOPE

(71) Applicant: OLYMPUS CORPORATION, Hachioji-shi, Tokyo (JP)

(72) Inventors: Takahiro Amanai, Hachioji (JP); Ayami Imamura, Hachioji (JP); Shinichi Mihara, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 388 days.

(21) Appl. No.: 15/452,821

(22) Filed: Mar. 8, 2017

(65) Prior Publication Data

US 2017/0336625 A1   Nov. 23, 2017

(30) Foreign Application Priority Data

May 19, 2016 (JP) ................................ 2016-100500

(51) Int. Cl.
*G02B 27/00* (2006.01)
*A61B 1/04* (2006.01)
(Continued)

(52) U.S. Cl.
CPC ........ *G02B 27/005* (2013.01); *A61B 1/00096* (2013.01); *A61B 1/041* (2013.01);
(Continued)

(58) Field of Classification Search
CPC .. A61B 1/041; A61B 1/00096; G02B 27/005; G02B 27/0062; G02B 13/001;
(Continued)

(56) References Cited

U.S. PATENT DOCUMENTS

| 5,724,190 A | * | 3/1998 | Tachihara | ................ G02B 9/12 359/661 |
| 2007/0014025 A1 | * | 1/2007 | Yokoyama | ......... G02B 13/0095 359/642 |

(Continued)

FOREIGN PATENT DOCUMENTS

JP   2004312239 A   11/2004

*Primary Examiner* — John P Leubecker
(74) *Attorney, Agent, or Firm* — Holtz, Holtz & Volek PC

(57) ABSTRACT

An image pickup apparatus includes an image forming optical system having an aperture stop, a first lens, and a second lens, and an imager having a light-receiving surface that is curved to be concave toward the image forming optical system, and a relative partial dispersion for a medium of the first lens differs from a relative partial dispersion for a medium of the second lens, and when a straight line indicated by $\theta gF_{LA} = \alpha \times \upsilon d_{LA} + \beta_{LA}$ (where $\alpha = -0.00163$) has been set, $\theta gF_{LA}$ and $\upsilon d_{LA}$ for the medium of the first lens are included in both of an area determined by the following conditional expression (1) and an area determined by the following conditional expression (2), and the following conditional expression (3) is satisfied:

$0.68 < \beta_{LA}$ (1), $\upsilon d_{LA} < 50$ (2), and $0 < |f/R_{img}| \leq 1.5$ (3).

20 Claims, 13 Drawing Sheets

(51) Int. Cl.
*G02B 13/00* (2006.01)
*G02B 23/24* (2006.01)
*A61B 1/00* (2006.01)

(52) U.S. Cl.
CPC ....... *G02B 13/001* (2013.01); *G02B 23/2461* (2013.01); *G02B 23/2484* (2013.01); *G02B 27/0062* (2013.01)

(58) Field of Classification Search
CPC .................. G02B 13/003; G02B 13/0035; G02B 23/243; G02B 23/2461; G02B 23/2484
See application file for complete search history.

(56) References Cited

U.S. PATENT DOCUMENTS

| | | | |
|---|---|---|---|
| 2007/0091458 A1* | 4/2007 | Asami | G02B 9/12 |
| | | | 359/680 |
| 2014/0233112 A1* | 8/2014 | Harada | A61B 1/00096 |
| | | | 359/781 |
| 2015/0185437 A1* | 7/2015 | Suzuki | G02B 13/04 |
| | | | 359/754 |
| 2015/0323761 A1* | 11/2015 | Chen | H01L 27/14607 |
| | | | 348/241 |
| 2016/0178885 A1* | 6/2016 | Harada | G02B 27/0025 |
| | | | 359/753 |
| 2017/0224201 A1* | 8/2017 | Yamamoto | A61B 1/00163 |
| 2018/0095256 A1* | 4/2018 | Iwamoto | G02B 13/18 |

* cited by examiner

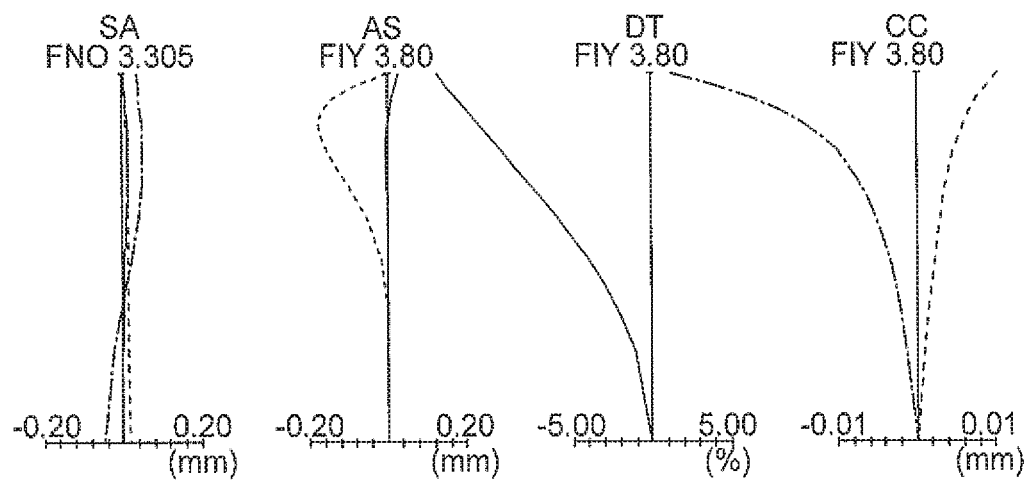
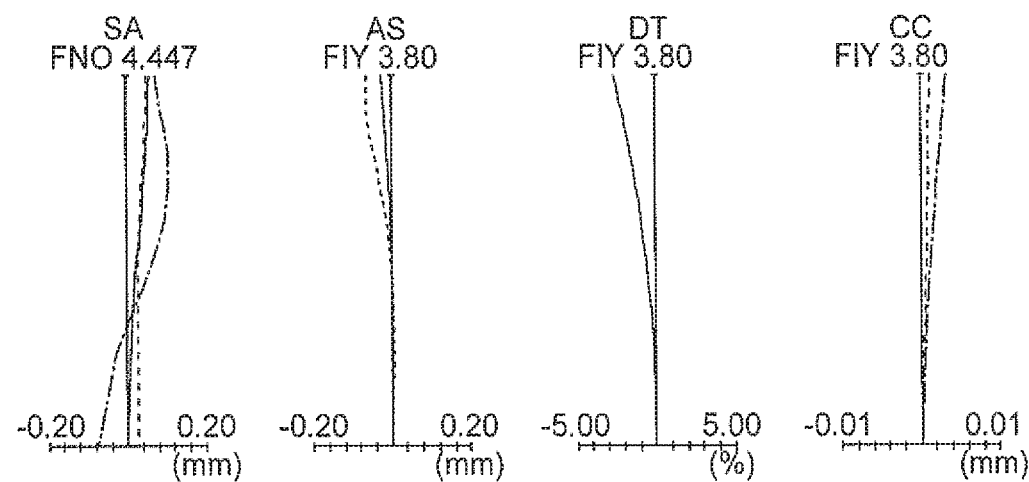
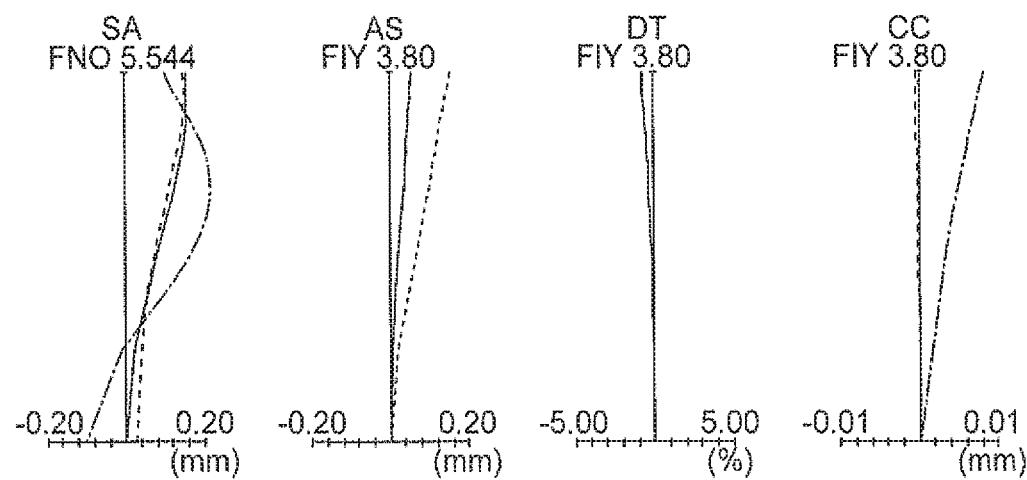

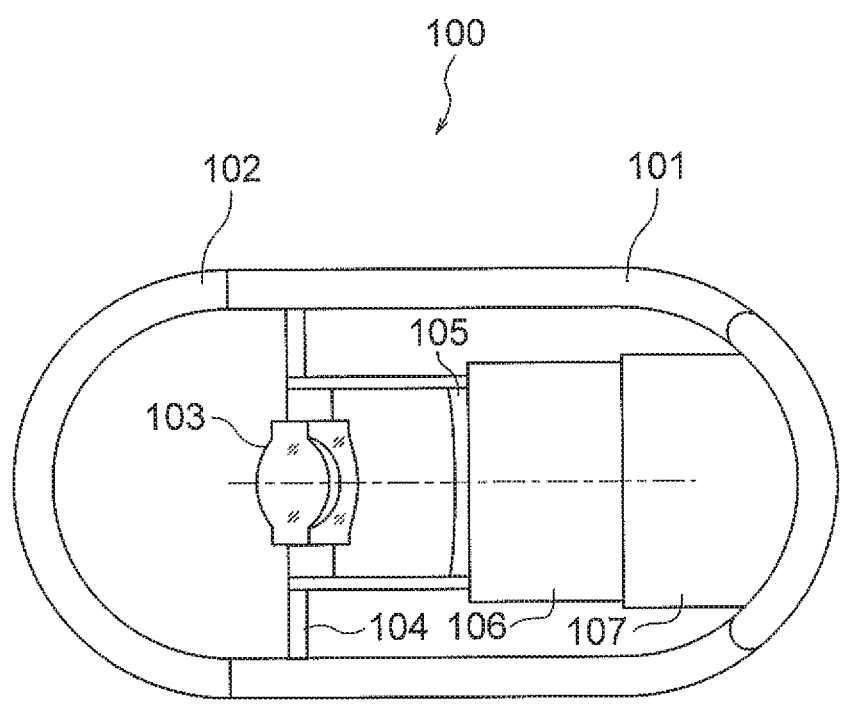

IMAGE PICKUP APPARATUS WHICH CORRECTS CHROMATIC ABERRATION IN A WIDE WAVELENGTH RANGE, AND CAPSULE ENDOSCOPE

CROSS-REFERENCE TO RELATED APPLICATION

The present application is based upon and claims the benefit of priority from the prior Japanese Patent Application No. 2016-100500 filed on May 19, 2016; the entire contents of which are incorporated herein by reference.

BACKGROUND OF THE INVENTION

Field of the Invention

The present invention relates to an image pickup apparatus and a capsule endoscope.

Description of the Related Art

As an optical system which forms a curved optical image in which a chromatic aberration is corrected, an optical system of an image pickup apparatus described in Japanese Patent Application Laid-open Publication No. 2004-312239 has been proposed. This optical system includes an achromatic lens made of two lenses. A half angle of view in this optical system is 30 degrees. Moreover, in this optical system, the chromatic aberration is corrected in a wavelength range of 460 nm to 630 nm.

SUMMARY OF THE INVENTION

An image pickup apparatus according to at least some of the embodiments of the present invention includes an image forming optical system which includes an aperture stop that sets an axial light beam, a first lens, and a second lens, and an imager which is disposed on an image side of the image forming optical system, and has a light-receiving surface which is not flat and is curved to be concave toward the image forming optical system, wherein a relative partial dispersion for a medium of the first lens differs from a relative partial dispersion for a medium of the second lens, and in a rectangular coordinate system in which a horizontal axis is let to be $\upsilon d_{LA}$ and a vertical axis is let to be $\theta gF_{LA}$, when a straight line indicated by $\theta gF_{LA} = \alpha \times \upsilon d_{LA} + \beta_{LA}$ (where $\alpha = -0.00163$) has been set, $\theta gF_{LA}$ and $\upsilon d_{LA}$ for the medium of the first lens are included in both of an area determined by the following conditional expression (1) and an area determined by the following conditional expression (2), and the following conditional expression (3) is satisfied:

$$0.68 < \beta_{LA} \quad (1)$$

$$\upsilon d_{LA} < 50 \quad (2), \text{ and}$$

$$0 < |f/R_{img}| \leq 1.5 \quad (3)$$

where, $\theta gF_{LA}$ denotes the relative partial dispersion $(ng_{LA} - nF_{LA})/(nF_{LA} - nC_{LA})$ for the medium of the first lens, $\upsilon d_{LA}$ denotes Abbe number $(nd_{LA} - 1)/(nF_{LA} - nC_{LA})$ for the medium of the first lens, $nd_{LA}$, $nC_{LA}$, $nF_{LA}$, and $ng_{LA}$ denote refractive indices of the medium of the first lens for a d-line, a C-line, an F-line, and a g-line respectively, $R_{img}$ denotes a radius of curvature of a virtual spherical surface including a surface apex and a point at which a principal light ray with the maximum image height of the image forming optical system and the light-receiving surface intersect, when a point of intersection of the optical axis and the light-receiving surface is let to be the surface apex, and f denotes a focal length of the image forming optical system for the d-line, and when the focal length of the image forming optical system is variable, conditional expression (3) is a conditional expression in a state at a wide angle end.

Moreover, a capsule endoscope according to at least some of the embodiments of the present invention includes the abovementioned image pickup apparatus, an illuminating portion, and a cover portion having a dome shape disposed on an object side of both the image forming optical system and the illuminating portion.

BRIEF DESCRIPTION OF THE DRAWINGS

FIG. 5A, FIG. 58, and FIG. 5C are cross-sectional views of an image pickup apparatus according to an example 5;

FIG. 6A, FIG. 6B, FIG. 6C, FIG. 6D, FIG. 6E, FIG. 6F, FIG. 6G, FIG. 6H, FIG. 6I, FIG. 6J, FIG. 6K, and FIG. 6L are aberration diagrams of the image pickup apparatus according to the example 5;

FIG. 12 is a diagram showing a schematic arrangement of a capsule endoscope; FIG. 13A is a diagram showing an example in which the car-mounted camera is mounted on outside of a car, and FIG. 13B is a diagram showing an example in which the car-mounted camera is mounted inside the car.

DETAILED DESCRIPTION OF THE INVENTION

Figure 1A:
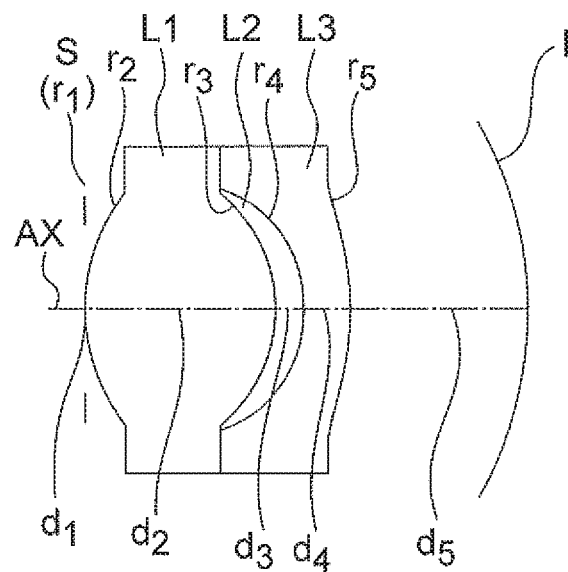
FIG. 1A is a cross-sectional view of an image pickup apparatus according to an example 1.
Figures 1B, 1C, 1D, 1E:
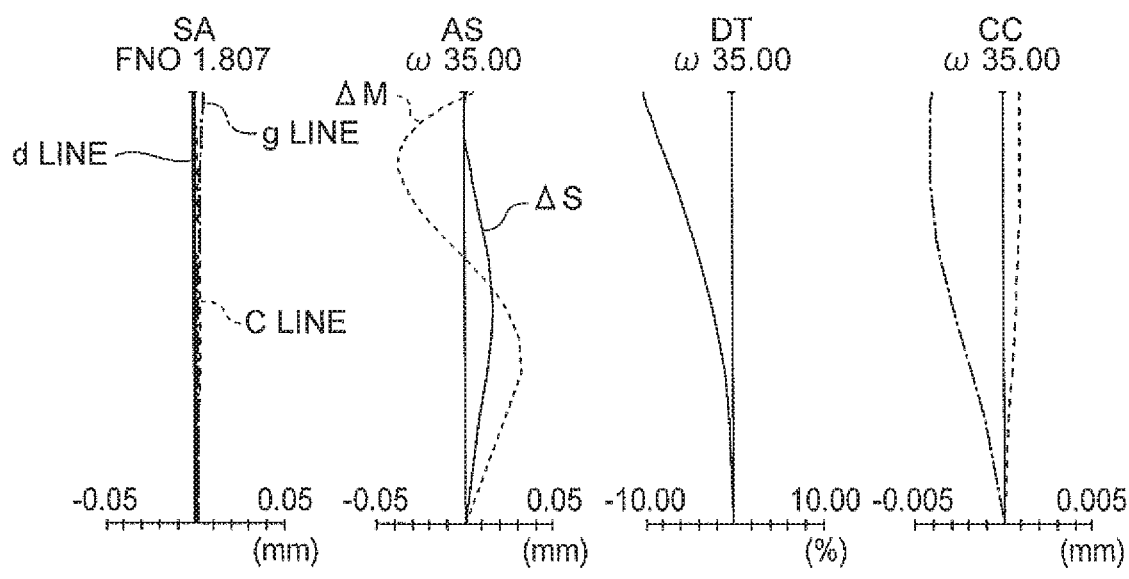
FIG. 1B, FIG. 1C, FIG. 1D, and FIG. 1E are aberration diagrams.
Figure 2A:
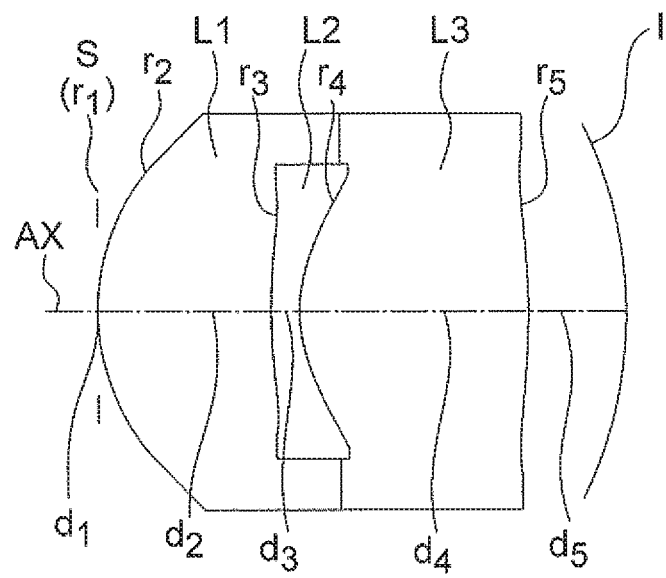
FIG. 2A is a cross-sectional view of an image pickup apparatus according to an example 2.
Figures 2B, 2C, 2D, 2E:
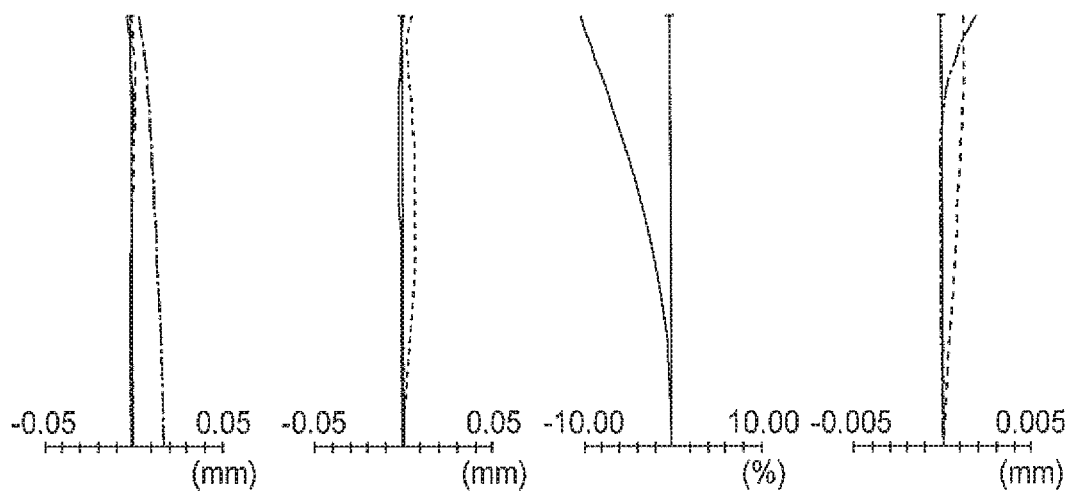
FIG. 2B, FIG. 2C, FIG. 2D, and FIG. 2E are aberration diagrams.
Figure 3A:
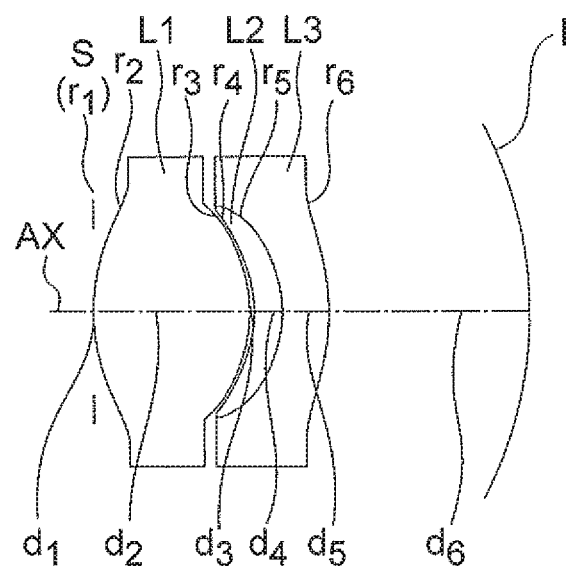
FIG. 3A is a cross-sectional view of an image pickup apparatus according to an example 3.
Figures 3B, 3C, 3D, 3E:
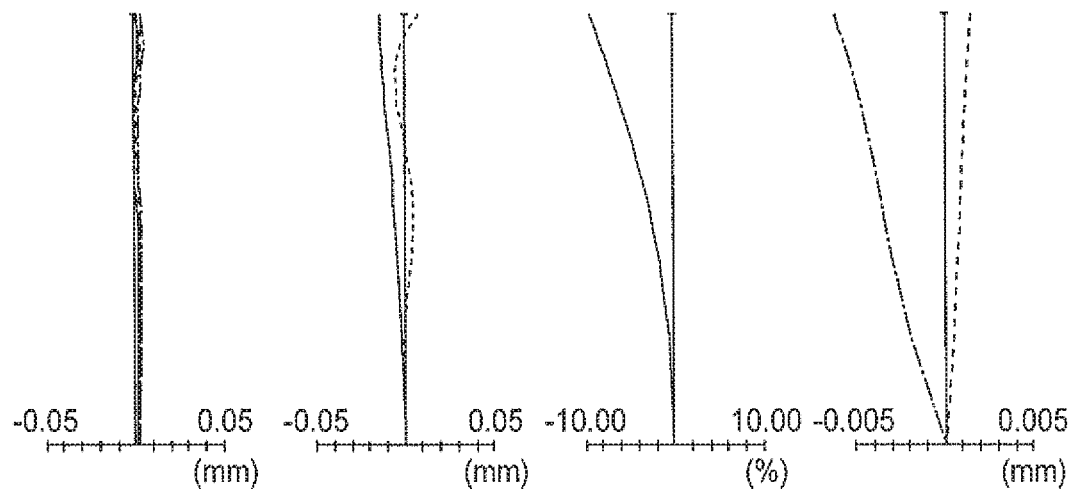
FIG. 3B, FIG. 3C, FIG. 3D, and FIG. 3E are aberration diagrams.
Figure 4A:
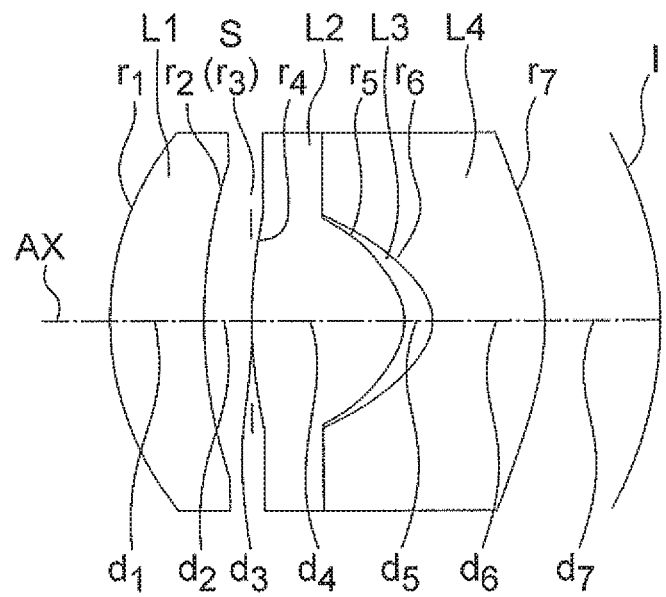
FIG. 4A is a cross-sectional view of an image pickup apparatus according to an example 4.
Figures 4B, 4C, 4D, 4E:
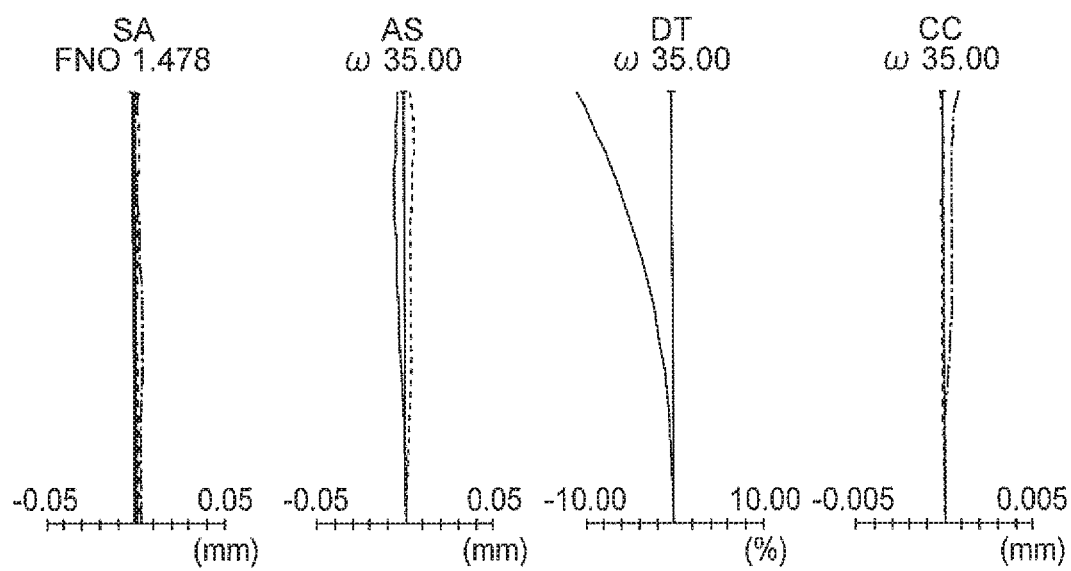
FIG. 4B, FIG. 4C, FIG. 4D, and FIG. 4E are aberration diagrams.

Exemplary embodiments and examples of an image pickup apparatus and a capsule endoscope according to the present invention will be described below in detail by referring to the accompanying diagrams. However, the present invention is not limited to the embodiments and examples described below.

An image pickup apparatus of the present embodiment includes an image forming optical system which includes an aperture stop that sets an axial light beam, a first lens, and a second lens, and an imager which is disposed on an image side of the image forming optical system, and has a light-receiving surface which is not flat and is curved to be concave toward the image forming optical system, wherein a relative partial dispersion for a medium of the first lens differs from a relative partial dispersion for a medium of the second lens, and in a rectangular coordinate system in which a horizontal axis is let to be $\nu d_{LA}$ and a vertical axis is let to be $\theta gF_{LA}$, when a straight line indicated by $\theta gF_{LA} = \alpha \times \nu d_{LA} + \beta_{LA}$ (where $\alpha = -0.00163$) has been set, $\theta gF_{LA}$ and $\nu d_{LA}$ for the medium of the first lens are included in both of an area determined by the following conditional expression (1) and an area determined by the following conditional expression (2), and the following conditional expression (3) is satisfied:

$$0.68 < \beta_{LA} \quad (1),$$

$$\nu d_{LA} < 50 \quad (2), \text{ and}$$

$$0 < |f/R_{img}| 1.5 \quad (3)$$

where, $\theta gF_{LA}$ denotes the relative partial dispersion $(ng_{LA} - nF_{LA})/(nF_{LA} - nC_{LA})$ for the medium of the first lens, $\nu d_{LA}$ denotes Abbe number $(nd_{LA} - 1)/(nF_{LA} - nC_{LA})$ for the medium of the first lens, $nd_{LA}$, $nC_{LA}$, $nF_{LA}$, and $ng_{LA}$ denote refractive indices of the medium of the first lens for a d-line, a C-line, an F-line, and a g-line respectively, $R_{img}$ denotes a radius of curvature of a virtual spherical surface including a surface apex and a point at which a principal light ray with the maximum image height of the image forming optical system and the light-receiving surface intersect, when a point of intersection of the optical axis and the light-receiving surface is let to be the surface apex, and f denotes a focal length of the image forming optical system for the d-line, and when the focal length of the image forming optical system is variable, conditional expression (3) is a conditional expression in a state at a wide angle end.

The image pickup apparatus of the present embodiment includes the image forming optical system and the imager. The image forming optical system has the aperture stop which sets the axial light beam, the first lens, and the second lens. The first lens and the second lens can be arranged in any order. The first lens may be positioned on the object side of the second lens or on the image side of the second lens. Moreover, the first lens and the second lens may be adjacent or another lens may have been disposed between the first lens and the second lens.

When falling below a lower limit value of conditional expression (1), it becomes difficult to correct adequately a secondary spectrum, or in other words, an aberration for the g-line that has remained when achromatization was carried out for the F-line and the C-line. In this case, it becomes difficult to correct adequately a chromatic aberration of magnification in the secondary spectrum, or to correct adequately a longitudinal chromatic aberration in the secondary spectrum. Therefore, an acutance of an image is susceptible to be deteriorated.

By satisfying conditional expression (1), it is possible to carry out the correction of the chromatic aberration of magnification or the correction of the longitudinal chromatic aberration adequately for the g-line, the F-line, and the C-line. As result, it is possible to correct a chromatic aberration in a wide wavelength-range.

When conditional expression (2) is satisfied, in a case in which the first lens is a positive lens, it is possible to correct the chromatic aberration favorably, and in addition, it is possible to correct other aberrations adequately. Moreover, in a case in which the first lens is a negative lens, achromatization for the F-line and the C-line becomes easier.

By satisfying conditional expression (3), it is possible to carryout small-sizing of the optical system and suppressing an occurrence of the chromatic aberration concurrently. This will be described below.

For instance, when the optical system is made small-sized, a positive refractive power in the optical system becomes large. The positive refractive power in the optical system is attributed to a positive lens. Therefore, when the positive refractive power in the optical system becomes large, the refractive power of the positive lens also becomes large.

As the positive refractive power of the positive lens becomes large, an amount of the chromatic aberration increases. For suppressing the occurrence of the chromatic aberration, it is preferable to use a medium having as small dispersion as possible for the positive lens. In such manner, from a viewpoint of correcting the chromatic aberration, the dispersion of the medium that can be used for the positive lens is restricted to a certain magnitude.

As the magnitude of dispersion that can be selected is restricted, the refractive index that can be selected is also restricted to a certain magnitude. The magnitude of the refractive index of the medium affects a magnitude of Petzval's sum. Therefore, when the magnitude of the refractive index of the medium that can be used for the positive lens is restricted to a certain magnitude, options for a method for suppressing the magnitude of Petzval's sum are reduced. The magnitude of Petzval's sum indicates a magnitude of curvature of field. Therefore, when the refractive index of the medium that can be used for the positive lens is restricted to certain magnitude, options for a method for correcting the curvature of field are reduced.

When the magnitude of the refractive index of the medium that can be used for the positive lens is restricted to a certain magnitude, it becomes difficult to select freely the magnitude of the refractive index of the medium. Consequently, the curvature of field cannot be corrected adequately. In this case, the curvature of field is to be corrected by another method. As another method, a method of correcting the curvature of field by changing a curvature of a lens surface is available. However, in this method, a coma is deteriorated remarkably.

Conditional expression (3) indicates that the occurrence of the curvature of field is acceptable to certain extent. Therefore, even when the magnitude of the refractive index of the medium that can be used for the positive lens is restricted to a certain extent, it is not necessary any more to correct the curvature of field by changing the curvature of a lens surface forcibly. As a result, the coma is not deteriorated remarkably. Moreover, since the coma is not deteriorated remarkably, it is possible to correct the other aberrations favorably.

When the occurrence of the curvature of field is acceptable to certain extent, it is not necessary anymore to correct the curvature of field by combining the positive lens and the negative lens. Consequently, it is possible to make the optical system small-sized.

By satisfying conditional expression (3), it is possible to make the optical system small-sized and to suppress the occurrence of the chromatic aberration in the wide wavelength range, and in addition, it is possible to correct favorably various aberrations such as the coma.

In such manner, by satisfying conditional expressions (1), (2), and (3) it is possible to realize an image pickup apparatus in which the chromatic aberration is corrected favorably in the wide wavelength range, while being small-sized.

It is more preferable that the following conditional expression (1-1) be satisfied instead of conditional expression (1).

$$0.68 < \beta_{LA} < 0.9 \quad (1\text{-}1)$$

It is more preferable that the following conditional expression (2-1) be satisfied instead of conditional expression (2).

$$3 < \upsilon d_{LA} < 50 \quad (2\text{-}1)$$

It is more preferable that the following conditional expression (3-1) be satisfied instead of conditional expression (3).

$$0.05 < |f/R_{img}| \leq 1 \quad (3\text{-}1)$$

In a case in which, the image forming optical system is a single focal length optical system, it is even more preferable that the following conditional expression (3-2) be satisfied instead of conditional expression (3).

$$0.5 < |f/R_{img}| \leq 1 \quad (3\text{-}2)$$

In the image pickup apparatus of the present embodiment, in another rectangular coordinate system in which a horizontal axis is let to be $\upsilon d_{LA}$ and a vertical axis is let to be $\theta hg_{LA}$, when a straight line indicated by $\theta hg_{LA} = \alpha hg \times \upsilon d_{LA} + \beta hg_{LA}$ (where $\alpha hg = -0.00225$) has been set, it is preferable that $\theta hg_{LA}$ and $\upsilon d_{LA}$ for the medium of the first lens be included in both of an area determined by the following conditional expression (4) and an area determined by the following conditional expression (2):

$$0.65 < \beta hg_{LA} \quad (4), \text{ and}$$

$$\upsilon d_{LA} < 50 \quad (2)$$

where, $\theta hg_{LA}$ denotes a relative partial dispersion $(nh_{LA} - ng_{LA})/(nF_{LA} - nC_{LA})$ for the medium of the first lens, and $nh_{LA}$ denotes a refractive index for an h-line of the medium of the first lens.

When falling below a lower limit value of conditional expression (4), it becomes difficult to correct adequately the secondary spectrum, or in other words, an aberration for the h-line that has remained when the achromatization was carried out for the F-line and the C-line. In this case, it becomes difficult to correct adequately the chromatic aberration of magnification in the secondary spectrum, or to correct adequately the longitudinal chromatic aberration in the secondary spectrum. Therefore, the acutance of an image is susceptible to be deteriorated. Particularly, a chromatic blurring of magenta is susceptible to occur in an outline portion of image.

By satisfying conditional expression (4), it is possible to carry out the correction of the chromatic aberration of magnification or the correction of the longitudinal chromatic aberration adequately for the h-line, the F-line, and the C-line. As a result, it is possible to correct the chromatic aberration in a wide wavelength range.

It is more preferable that the following conditional expression (4-1) be satisfied instead of conditional expression (4).

$$0.65 < \beta hg_{LA} < 0.9 \quad (4\text{-}1)$$

In the image pickup apparatus of the present embodiment, it is preferable that the first lens and the second lens be cemented.

By making such arrangement, not only it is possible to correct favorably a paraxial chromatic aberration such as the longitudinal chromatic aberration but also it is possible to correct favorably the chromatic aberration of magnification and the chromatic aberration of higher order. A wavelength interval difference in a spherical aberration and a wavelength interval difference in the coma are examples of the chromatic aberration of higher order.

The wavelength interval difference in this case refers to a difference in an amount of aberration of two wavelengths. In a case of a plurality of wavelengths, the wavelength interval difference is a difference in an amount of aberration of two arbitrary wavelengths.

Even when a light ray before being incident on an optical system is one light ray, the light rays are separated according to wavelength due to dispersion. Therefore, a plurality of light rays reaches an imager. Coordinates of a point of intersection of light rays and an image pickup surface differ for each wavelength. When coordinate of a certain light ray is set to be reference, there is a shift between the coordinate which is set to be reference and coordinate of a point of intersection of a light ray of the other wavelength. The wavelength interval difference corresponds to an amount of shift between the coordinates.

For cementing, it is preferable to use a method of fixing two lenses by a cementing material or a method of fixing two lenses by curing a resin. The method of fixing two lenses by curing a resin will be described later.

It is preferable to make an arrangement such that the relative partial dispersion for the first lens and the relative partial dispersion for the second lens differ substantially. By making such arrangement, it is possible to correct favorably the paraxial chromatic aberration, the chromatic aberration of magnification and the chromatic aberration of higher order.

By cementing the first lens and the second lens, it is possible to improve a manufacturing accuracy.

In the image pickup apparatus according to the present embodiment, it is preferable that the first lens be a resin lens, and the first lens be cured upon bringing in close contact with a refracting surface of the second lens.

By doing so, it is possible to reduce a surface shape error and a decentering error. Furthermore, it is possible to make the lens thin.

For curing upon bringing in close contact, it is preferable to use a liquid resin such as an ultraviolet-cured resin. An ultraviolet-cured resin is an example of a lens material for the first lens. A desired amount of the ultraviolet-cured resin is to be discharged on to the refracting surface of the second lens. Accordingly, the ultraviolet-cured resin assumes a state of being in contact with the refracting surface of the second lens. Out of the surfaces of the ultraviolet-cured resin, a surface in contact with the refracting surface of the second lens becomes one refracting surface of the first lens.

A mold is disposed at a position facing the second lens holding the ultraviolet-cured resin. The mold is pressed against the ultraviolet-cured resin. The ultraviolet-cured resin is in a state of being held between the mold and the second lens. In this state, ultraviolet rays are irradiated from the second lens side. Accordingly, the ultraviolet-cured resin is cured.

The mold has a molding surface. The molding surface is a surface in contact with the ultraviolet-cured resin. A shape of the molding surface is same as a shape of the other refracting surface of the first lens. Out of the surfaces of the ultraviolet-cured resin, a surface in contact with the molding surface is the other refracting surface of the first lens.

In such manner, in curing upon bringing in close contact, one refracting surface of the first lens is formed by the refracting surface of the second lens, and the other refracting surface of the first lens is formed by the molding surface of the mold.

The material of the first lens is not restricted to the ultraviolet-cured resin. The method for curing is also not restricted to by irradiating the ultraviolet rays.

In the image pickup apparatus according to the present embodiment, it is preferable that a sign of a focal length of the first lens differ from a sign of a focal length of the second lens.

The second lens has the chromatic aberration. The chromatic aberration in the second lens occurs between the C-line and the F-line, between the C-line and the g-line, and between the F-line and the g-line. Even in the first lens, the chromatic aberration similarly as in the second lens occurs. Therefore, the sign of the focal length of the first lens is let to differ from the sign of the focal length of the second lens. By making such arrangement, it is possible to reverse a direction in which the chromatic aberration occurs in the first lens with respect to a direction in which the chromatic aberration occurs in the second lens. Consequently, it is possible to cancel substantially the chromatic aberration in the second lens by the chromatic aberration in the first lens.

In the image pickup apparatus according to the present embodiment, it is preferable that the first lens have at least one aspheric surface.

By making such arrangement, it is possible to enhance an effect of correcting a monochromatic spherical aberration.

Factors having a strong effect on the chromatic aberration of higher order are an aspheric surface component and dispersion characteristics of the first lens. The aspheric surface component is an amount indicating as to how much the aspheric surface is displaced from a spherical surface. The aspheric surface component and the dispersion characteristics of the first lens have a determinate relation with the chromatic aberration of higher order. When a cemented surface is let to be an aspheric surface, since the aspheric surface becomes an interface formed by two media having different dispersion, the effect of correcting the chromatic aberration of higher order is further improved.

In the image pickup apparatus according to the present embodiment, it is preferable that the aspheric surface of the first lens be an aspheric surface for which an absolute value of a curvature becomes smaller gradually toward a direction of separating away from the optical axis.

By making such arrangement, it is possible to suppress the occurrence of the chromatic aberration of higher order. Particularly, it is preferable to make the absolute value of the curvature of the refracting surface small at a position at which a height of a principal light ray and a height of a marginal light ray at image height become large. By making such arrangement, it becomes easy to reduce the occurrence of the chromatic aberration of higher order.

In the image pickup apparatus of the present embodiment, it is preferable that the aspheric surface of the first lens be an aspheric surface having a point of inflection in an effective area on a cross-sectional surface including an axial principal light ray.

By making such arrangement, in the cross-sectional surface including the axial principal light ray, the point of inflection exists at an inner side of an effective area of a lens surface. Therefore, it becomes easier to control the occurrence of the chromatic aberration of higher order. Moreover, at the same time, it becomes easy to optimize an angle of the principal light ray with respect an image plane and to correct various off-axis aberrations.

The effective area in this case refers to an area on the lens surface, and is an area determined by all light rays passing through the lens surface. All the light rays passing through the lens surface refers to light rays that reach an area in which an image can be picked up, of the imager, and light rays that contribute to image formation.

The chromatic aberration of higher order refers to the difference in wavelength intervals in various aberrations. Examples of the various aberrations are the spherical aberration, the coma, an astigmatism, the curvature of field, and a distortion.

In the image pickup apparatus of the present embodiment, it is preferable that the aperture stop be disposed on an object side of the first lens.

Other factors having a strong effect on the chromatic aberration of higher order are a position of the first lens and a position of the aperture stop. A relation of the position of the first lens and the position of the aperture stop is associated with the chromatic aberration of higher order (chromatic coma and chromatic aberration of magnification). By disposing the aperture stop on the object side of the first lens, it is possible to enhance an effect of correcting the chromatic aberration of higher order.

In the image pickup apparatus of the present embodiment, it is preferable that from among lens surfaces in the image forming optical system, a lens surface positioned nearest to image be a surface which is convex toward the image side.

In the image pickup apparatus of the present embodiment, the imager has the light-receiving surface that is not flat and is curved to be concave toward the image forming optical system. Therefore, for the imager, the lens surface positioned nearest to image is to be made a surface which is convex toward the image side. By making such arrangement, an arrangement of lenses in the image forming optical system becomes a concentric arrangement. Therefore, it is possible to carry out favorably the correction of an off-axis aberration such as an astigmatic difference and the coma. Letting the lens surface positioned nearest to image to be convex toward the image side is advantageous for correction of the off-axis aberration.

In the image pickup apparatus of the present embodiment, it is preferable that the following conditional expression (5) be satisfied:

$$0 \le |(Y_e/R_e)-(Y_{img}/R_{img})| < 0.3 \qquad (5)$$

where, $Y_e$ denotes a distance of a point at which a principal light ray at the maximum angle of view of the image forming optical system intersects a surface nearest to image of the image forming optical system from the optical axis, $R_e$ denotes a paraxial radius of curvature of a surface nearest to image out of lens surfaces in the image forming optical system, $Y_{img}$ denotes a distance of a point at which the principal light ray at the maximum angle of view of the image forming optical system intersects the light-receiving surface, and $R_{img}$ denotes the radius of curvature of a virtual spherical surface including a surface apex and a point at which a principal light ray with the maximum image height of the image forming optical system and the light-receiving surface intersect, when a point of intersection of the optical axis and the light-receiving surface is let to be the surface apex, and when the focal length of the image forming optical system is variable, conditional expression (5) is a conditional expression in the state at the wide angle end.

Conditional expression (5) regulates an appropriate ratio of a paraxial radius of curvature of the lens surface positioned nearest to image from among the lens surfaces in the image forming optical system and a radius of curvature of the virtual surface set near the light-receiving surface.

In the image pickup apparatus of the present embodiment, the occurrence of the curvature of field is acceptable to certain extent. Therefore, Petzval image plane in the image forming optical system is curved to be concave toward the image forming optical system. Moreover, the light-receiving surface of the imager is also curved to be concave toward the image forming optical system.

In this case, it is preferable to match a shape of the Petzval image plane and a shape of the light-receiving surface. When the Petzval image plane and the light-receiving surface cannot be matched, it is preferable to make an arrangement such that a divergence of the shape of the Petzval image plane and the shape of the light-receiving surface is not more than an acceptable value.

When the divergence of the shape of the Petzval image plane and the shape of the light-receiving surface becomes larger than the acceptable value, in the image forming optical system, the astigmatic difference is to be corrected. In the image forming optical system, the height of the principal light ray becomes high at the lens surface positioned nearest to image. Therefore, it becomes significant to satisfy conditional expression (5). By making so as not to exceed an upper limit value of conditional expression (5), it is possible to suppress an increase in the astigmatic difference.

It is more preferable that the following conditional expression (5-1) be satisfied instead of conditional expression (5).

$$0 \leq |(Y_e/R_e) - (Y_{img}/R_{img})| < 0.15 \qquad (5\text{-}1)$$

Accordingly, it is possible to exert further an effect of conditional expression (5).

In the image pickup apparatus of the present embodiment, it is preferable that the following conditional expression (6) be satisfied:

$$0.5 < |R_1/R_e| \leq 1.5 \qquad (6)$$

where, $R_1$ denotes a paraxial radius of curvature of a surface nearest to object out of the lens surfaces of the image forming optical system, and $R_e$ denotes the paraxial radius of curvature of a surface nearest to image out of the lens surfaces of the image forming optical system.

By satisfying conditional expression (6), it is possible to let the paraxial radius of curvature of the lens surface positioned nearest to object almost same as the paraxial radius of curvature of the lens surface positioned nearest to image. As a result, it is possible to correct the spherical aberration and astigmatism with a high level as well as in a balanced manner. When such correction is possible, an amount of each of the two aberrations that occur becomes small, and moreover, the amount of the two aberrations becomes almost equal.

When exceeding an upper limit value of conditional expression (6), the correction of the spherical aberration is susceptible to become difficult. When falling below a lower limit value of conditional expression (6), correction of astigmatism is susceptible to become difficult.

It is more preferable that the following conditional expression (6-1) be satisfied instead of conditional expression (6).

$$0.6 < ..R_1/R_e| \leq 1.2 \qquad (6\text{-}1)$$

Accordingly, it is possible to exert further the effect of conditional expression (6).

In the image pickup apparatus of the present embodiment, it is preferable that the following conditional expression (7) be satisfied:

$$0.5 < L_{1e}/TL \qquad (7)$$

where, $L_{1e}$ denotes an actual distance from a lens surface nearest to object on an optical axis of the image forming optical system up to a surface adjacent to a surface different from a cover glass, which is a surface positioned nearest to the light-receiving surface and adjacent to air, in the image forming optical system, and TL denotes an actual distance on the optical axis of the image forming optical system, from a lens surface nearest to object up to the light-receiving surface, and when the focal length of the image forming optical system is variable, conditional expression (7) is a conditional expression in the state at the wide angle end.

Conditional expression (7) regulates an appropriate ratio of the actual distance up to a predetermined lens surface from the lens surface positioned nearest to object in the image forming optical system and the actual distance up to the light-receiving surface from the lens surface positioned nearest to object in the image forming optical system. The predetermined lens surface is a surface adjacent to air positioned nearest to the light-receiving surface in the image forming optical system, which is a surface different from a cover glass. In other words, the predetermined lens surface is a lens surface positioned nearest to image from among the lens surfaces in the image forming optical system. Moreover, the actual distance is a distance on the optical axis of the image forming optical system, and is a distance not subjected to air conversion.

By satisfying conditional expression (7), since it is possible to have an image pickup apparatus of a small-sized optical system with a short back focus, it is more preferable.

It is more preferable that the following conditional expression (7-1) be satisfied instead of conditional expression (7).

$$0.5 < L_{1e}/TL < 0.96 \qquad (7\text{-}1)$$

Accordingly, it is possible to exert further the effect of conditional expression (7). Shortening the back focus so as not to fall below a lower limit value of conditional expression (7-1) is more advantageous for shortening the overall length of the optical system. Securing the back focus so as not to exceed an upper limit value of conditional expression (7-1) is advantageous for small-sizing of an optical system portion.

In the image pickup apparatus of the present embodiment, it is preferable that the following conditional expression (8) be satisfied:

$$0 < PS \times f < 1 \quad (8)$$

where,

PS denotes Petzval's sum for the image forming optical system, and

Petzval's sum PS is expressed by the following expression:

$$PS = \sum_{i=1}^{k} \frac{1}{n_i \times f_i}$$

where i denotes an order of lenses from the object side in the image forming optical system, k denotes the total number of lenses in the image forming optical system, $n_i$ denotes a refractive index of an $i^{th}$ lens for the d-line, $f_i$ denotes a focal length of the $i^{th}$ lens for the d-line, and f denotes the focal length of the image forming optical system for the d-line, and when the focal length of the image forming optical system is variable, conditional expression (8) is a conditional expression in the state at the wide angle end.

By satisfying conditional expression (8), it is possible to achieve an image pickup apparatus in which the further correction of curvature of field and small-sizing are accomplished, and hence it is more preferable.

It is more preferable that the following conditional expression (8-1) be satisfied instead of conditional expression (8).

$$0.07 < PS \times f < 0.9 \quad (8-1)$$

In the image pickup apparatus of the present embodiment, it is preferable that the following conditional expression (9) be satisfied:

$$PS \times EXP < 0 \quad (9)$$

where,

PS denotes the Petzval's sum for the image forming optical system and

Petzval's sum PS is expressed by the following expression:

$$PS = \sum_{i=1}^{k} \frac{1}{n_i \times f_i}$$

where i denotes the order of lenses from the object side in the image forming optical system, k denotes the total number of lenses in the image forming optical system, $n_i$ denotes the refractive index of an $i^{th}$ lens for the d-line, $f_i$ denotes the focal length of the $i^{th}$ lens for the d-line, and EXP denotes a distance along the optical axis from the light-receiving surface up to a paraxial exit pupil position, and is let to have a negative sign when the paraxial exit pupil position is on the object side of the light-receiving surface, and when the focal length of the image forming optical system is variable, conditional expression (9) is a conditional expression in the state at the wide angle end.

By satisfying conditional expression (9), it is possible to achieve an image pickup apparatus of a small-sized optical system in which the curvature of field is corrected further, and a position of an exit pupil is near the image plane.

It is more preferable that the following conditional expression (9-1) be satisfied instead of conditional expression (9).

$$-1.5 < PS \times EXP < 0 \quad (9-1)$$

In the image pickup apparatus of the present embodiment, in another rectangular coordinate system in which a horizontal axis is let to be $\upsilon d_{LB}$ and a vertical axis is let to be $\theta gF_{LB}$, when a straight line indicated by $\theta gF_{LB} = \alpha \times \upsilon d_{LB} + \beta_{LB}$ (where $\alpha = -0.00163$) has been set, it is preferable that $\theta gF_{LB}$ and $\upsilon d_{LB}$ for the medium of the second lens be included in an area determined by the following conditional expression (10):

$$P_{LB} < 0.67 \quad (10)$$

where, $\theta gF_{LB}$ denotes a relative partial dispersion $(ng_{LB} - nF_{LB})/(nF_{LB} - nC_{LB})$ for the medium of the second lens, $\upsilon d_{LB}$ denotes Abbe number $(nd_{LB} - 1)/(nF_{LB} - nC_{LB})$ for the medium of the second lens, $nd_{LB}$, $nC_{LB}$, $nF_{LB}$, and $ng_{LB}$ denote refractive indices of the medium of the second lens for a d-line, a C-line, an F-line, and a g-line respectively.

By satisfying conditional expression (10), it is possible to correct favorably the chromatic aberration due to the secondary spectrum. When exceeding an upper limit value of conditional expression (10), the correction of the chromatic aberration due to the secondary spectrum is susceptible to be inadequate.

By satisfying conditional expression (1) and conditional expression (10), it is possible to make large the difference between the relative partial dispersion for the medium for the first lens and the relative partial dispersion for the medium for the second lens. As a result, it is possible to carry out adequately the correction of the chromatic aberration due to the secondary spectrum.

It is more preferable that the following conditional expression (10-1) be satisfied instead of conditional expression (10).

$$0.60 < \beta_{LB} < 0.67 \quad (10-1)$$

By making so as not to fall below a lower limit value of conditional expression (10-1), it becomes easy to suppress the correction of the secondary spectrum from becoming excessive.

In the image pickup apparatus of the present embodiment, in another rectangular coordinate system in which a horizontal axis is let to be $\upsilon d_n$ and a vertical axis is let to be $\theta hg_n$, when a straight line indicated by $\theta hg_{LB} = \alpha hg \times \upsilon d_{LB} + \beta hg_{LB}$ (where $\alpha hg = -0.00225$) has been set, it is preferable that $\theta hg_{LB}$ and $\upsilon d_{LB}$ for the medium of the second lens be included in an area determined by the following conditional expression (11):

$$\beta hg_{LB} < 0.64 \quad (11)$$

where, $\theta hg_{LB}$ denotes a relative partial dispersion $(nh_{LB} - ng_{LB})/(nF_{LB} - nC_{LB})$ for the medium of the second lens, and $nh_{LB}$ denotes a refractive index for an h-line of the medium of the second lens.

By satisfying conditional expression (11), it is possible to correct favorably the chromatic aberration due to the secondary spectrum. When exceeding an upper limit value of conditional expression (1), the correction of the chromatic aberration due to the secondary spectrum is susceptible to be inadequate.

By satisfying conditional expression (4) and conditional expression (11), it is possible to make large the difference between the relative partial dispersion for the medium of the first lens and the relative partial dispersion for the medium of the second lens. As a result, it is possible to carry out adequately the correction of the chromatic aberration due to the secondary spectrum in magenta color.

It is more preferable that the following conditional expression (11-1) be satisfied instead of conditional expression (11).

$$0.60 < \beta h g_{LB} < 0.64 \qquad (11\text{-}1)$$

By making so as not fall below a lower limit value of conditional expression (11-1), it is easy to suppress the correction of the secondary spectrum from becoming excessive.

Examples of arrangement (hereinafter, 'arrangement examples') of the image forming optical system will be described below. Arrangement examples 1 and 3 include three lenses, and an arrangement example 2 includes two lenses.

It is preferable that an image forming optical system of the arrangement example 1 include a first lens, a second lens, and a third lens, and the first lens be positioned between the second lens and the third lens, and the first lens, the second lens, and the third lens be cemented in an effective area, and the second lens and the third lens be cemented outside the effective area.

It is preferable that an image forming optical system of the arrangement example 2 include a first lens and a second lens, and, the first lens and the second lens be cemented in an effective area, and an object-side lens surface of the second lens be convex toward the object side, and the second lens have a convex portion outside the effective area, and the convex portion protrude toward the object side from an apex of the object-side lens surface. The object-side lens surface of the second lens is a surface in contact with the first lens.

It is preferable that an image forming optical system of the arrangement example 3 include a first lens, a second lens, a third lens and an annular member, and an outer diameter of the first lens be smaller than an outer diameter of the second lens and an outer diameter of the third lens, and the first lens and the annular member be positioned between the second lens and the third lens, and the first lens, the second lens, and the third lens be cemented in an effective area, and the annular lens be positioned at an outer side of the first lens.

A method of curing a resin upon bringing in close contact can be used for manufacturing the image forming optical systems of arrangement examples 1 to 3. In this case, the arrangement examples 1 to 3 are appropriate as a means for maintaining a liquid resin before curing.

In the method of curing a resin upon bringing in close contact, a liquid resin such as an ultraviolet-cured resin is to be used as a lens material for the first lens. This resin is dripped on a refracting surface of the second lens. In a state of the resin held on the refracting surface of the second lens, the resin is held by a mold. Thereafter, ultraviolet rays are irradiated from the second lens side and the resin is cured.

By curing the resin, the first lens is formed. By doing so, it is possible to realize the formation of the first lens and a close contact between the first lens and the second lens.

When the image forming optical system includes the third lens, after having cured the resin, it is preferable to separate the mold from the resin, and to cement the third lens to the resin. By doing so, it is possible to realize the formation of the first lens, and close contact of the first lens, the second lens, and the third lens.

When the image forming optical system has a third lens, the resin may be held by the third lens, instead of holding by a mold. By curing the resin in this state, it is possible to realize the formation of the first lens, and close contact between the second lens and the third lens. In this case, it is not necessary anymore to cement the third lens to the first lens.

In the image pickup apparatus of the present embodiment, it is preferable that the first lens be formed of an energy-curable resin. It is preferable that the energy-curable resin be either an ultraviolet-cured resin or a thermosetting resin.

In the image pickup apparatus of the present embodiment, it is preferable that the first lens be a negative lens and the second lens be a positive lens.

In the image pickup apparatus of the present embodiment, it is preferable that the second lens be made of glass.

In the image pickup apparatus of the present embodiment, it is preferable that the image forming optical system include a third lens, and that the third lens be a positive lens.

In the image pickup apparatus of the present embodiment, it is preferable that the third lens be made of glass.

It is preferable that the image pickup apparatus of the present embodiment further include an illuminating portion, and a cover portion disposed on the object side of the image forming optical system.

By disposing the cover portion, it is possible to make an arrangement such that a distance between an object and the image forming optical system is not excessively close, and it is advantageous to let the object within a depth of field. Having the illuminating portion is advantageous for night photography and intracavitary photography.

In the image pickup apparatus of the present embodiment, it is preferable that the cover portion have a dome shape covering an object side of both the image forming optical system and the illuminating portion.

By making such arrangement, it is possible not to let a distance between an object and the illuminating portion to be excessively close, and it is possible to reduce whiteout of a photographic image.

A capsule endoscope of the present embodiment includes the image pickup apparatus, the illuminating portion, and the cover portion having a dome shape disposed on the object side of the image forming optical system and the illuminating portion.

The image pickup apparatus of each embodiment being advantageous for small-sizing, it is preferable to arrange as a capsule endoscope having an illuminating portion and the cover portion.

For each conditional expression, it is possible to change the upper limit value and the lower limit value as follows.

For conditional expression (3-2), it is more preferable to let the lower limit value to be 0.55, and 0.6 is even more preferable.

For conditional expressions (10) and (10-1), it is more preferable to let the lower limit value to be 0.62, and 0.63 is even more preferable. Moreover, for conditional expressions (10) and (10-1) it is more preferable to let the upper limit value to be 0.66, and 0.65 is even more preferable.

For conditional expressions (11) and (11-1), it is more preferable to let the lower limit value to be 0.61, and 0.62 is even more preferable. Moreover, for conditional expressions (11) and (11-1), it is more preferable to let the upper limit value to be 0.58, and 0.57 is even more preferable.

Examples of image pickup apparatuses according to certain aspects of the present invention, and the capsule endoscope will be described below in detail by referring to the accompanying diagrams. However, the present invention is not limited to the examples described below.

Figure 5A:
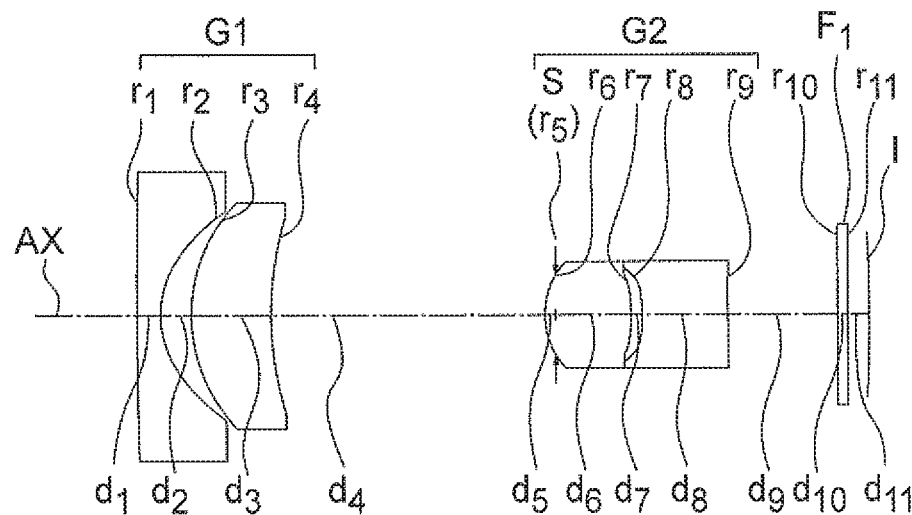
Figure 5B:
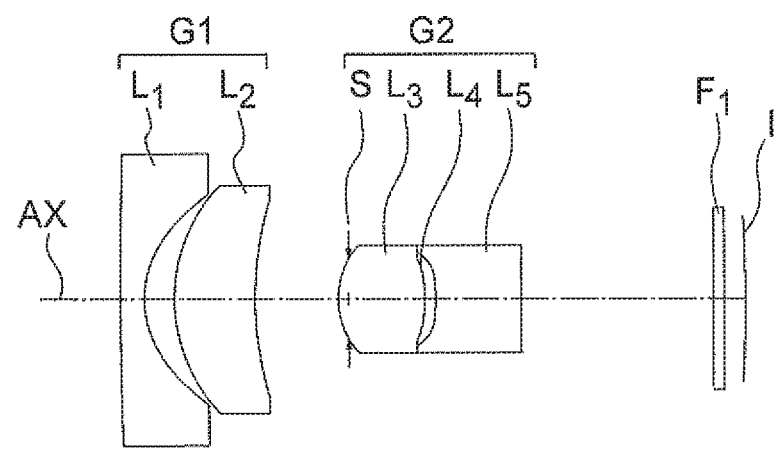
Figure 5C:
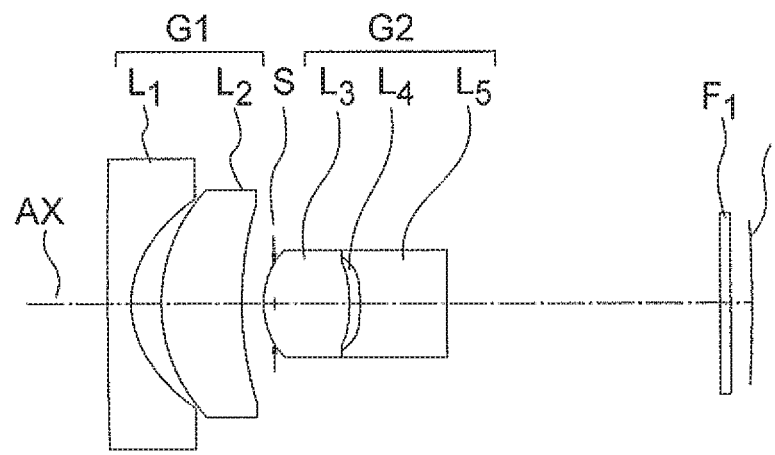

Cross-sectional diagrams will be described below. FIG. 1A, FIG. 2A, FIG. 3A, and FIG. 4A are lens cross-sectional views of an image pickup apparatus. FIG. 5A is a cross-sectional view in a state at a wide-angle end, FIG. 5B is a cross-sectional view in an intermediate focal length state, and FIG. 5C is a cross-sectional view in a state at a telephoto end.

Aberration diagrams will be described below. FIG. 13, FIG. 2B, FIG. 3B, and FIG. 4B show a spherical aberration (SA), FIG. 10, FIG. 2C, FIG. 3C, and FIG. 4C show an astigmatism (AS), FIG. 1D, FIG. 2D, FIG. 3D, and FIG. 4D show a distortion (DT), and FIG. 1E, FIG. 2E, FIG. 3E, and FIG. 4E show a chromatic aberration of magnification (CC).

FIG. 6A shows a spherical aberration (SA) at the wide angle end, FIG. 6B shows an astigmatism (AS) at the wide angle end, FIG. 6C shows a distortion (DT) at the wide angle end, and FIG. 6D shows a chromatic aberration of magnification (CC) at the wide angle end. FIG. 63 shows a spherical aberration (SA) in the intermediate focal length state, FIG. 6F shows an astigmatism (AS) in the intermediate focal length state, FIG. 6G shows a distortion (DT) in the intermediate focal length state, and FIG. 6H shows a chromatic aberration of magnification (CC) in the intermediate focal length state. FIG. 6I shows a spherical aberration (SA) at the telephoto end, FIG. 6J shows an astigmatism (AS) at the telephoto end, FIG. 6K shows a distortion (DT) at the telephoto end, and FIG. 6L shows a chromatic aberration of magnification (CC) at the telephoto end.

An image forming optical system of the image pickup apparatus according to the example 1 includes in order from an object side, a biconvex positive lens L1, a negative meniscus lens L2 having a convex surface directed toward an image side, and a negative meniscus lens L3 having a convex surface directed toward the image side. The biconvex positive lens L1, the negative meniscus lens L2, and the negative meniscus lens L3 are cemented.

An aperture stop S is disposed on the object side of the biconvex positive lens L1. A light-receiving surface (image pickup surface) I is a spherical surface, and is curved to be concave toward the object side. The negative meniscus lens L2 is the first lens. The negative meniscus lens L3 is the second lens.

An aspheric surface is provided to three surfaces namely, an object-side surface of the biconvex positive lens L1, a cemented surface of the negative meniscus lens L2 and the negative meniscus lens L3, and an image-side surface of the negative meniscus lens L3.

An image forming optical system of the image pickup apparatus according to the example 2 includes in order from an object side, a positive meniscus lens L1 having a convex surface directed toward the object side, a negative meniscus lens L2 having a convex surface directed toward the object side, and a biconvex positive lens L3. The positive meniscus lens L1, the negative meniscus lens L2, and the biconvex positive lens L3 are cemented.

An aperture stop S is disposed on the object side of the positive meniscus lens L1. A light-receiving surface (image pickup surface) I is a spherical surface, and is curved to be concave toward the object side. The negative meniscus lens L2 is the first lens. The biconvex positive lens L3 is the second lens.

An aspheric surface is provided to four surfaces namely, an object-side surface of the positive meniscus lens L1, a cemented surface of the positive meniscus lens L1 and the negative meniscus lens L2, a cemented surface of the negative meniscus lens L2 and the biconvex positive lens L3, and an image-side surface of the biconvex positive lens L3.

An image forming optical system of the image pickup apparatus according to the example 3 includes in order from an object side, a biconvex positive lens L1, a positive meniscus lens L2 having a convex surface directed toward an image side, and a negative meniscus lens L3 having a convex surface directed toward the image side. The positive meniscus lens L2 and the negative meniscus lens L3 are cemented.

An aperture stop S is disposed on the object side of the biconvex positive lens L1. A light-receiving surface (image pickup surface) I is a spherical surface, and is curved to be concave toward the object side. The positive meniscus lens L2 is the first lens. The negative meniscus lens L3 is the second lens.

An aspheric surface is provided to five surfaces namely, both side surfaces of the biconvex positive lens L1, an object-side surface of the positive meniscus lens L2, a cemented surface of the positive meniscus lens L2 and the negative meniscus lens L3, and an image-side surface of the negative meniscus lens L3.

An image forming optical system of the image pickup apparatus according to the example 4 includes in order from an object side, a positive meniscus lens L1 having a convex surface directed toward the object side, a biconvex positive lens L2, a positive meniscus lens L3 having a convex surface directed toward an image side, and a negative meniscus lens L4 having a convex surface directed toward the image side. The biconvex positive lens L2, the positive meniscus lens L3, and the negative meniscus lens L4 are cemented.

An aperture stop S is disposed between the positive meniscus lens L1 and the biconvex positive lens L2. A light-receiving surface (image pickup surface) I is a spherical surface, and is curved to be concave toward the object side. The positive meniscus lens L3 is the first lens. The negative meniscus lens L4 is the second lens.

An aspheric surface is provided to four surfaces namely, an object-side surface of the biconvex positive lens L2, a cemented surface of the biconvex positive lens L2 and the positive meniscus lens L3, a cemented surface of the positive meniscus lens L3 and the negative meniscus lens L4, and an image-side surface of the negative meniscus lens L4.

An image forming optical system of the image pickup apparatus according to the example 5 includes in order from an object side, a first lens unit G1 having a negative refractive power and second lens unit G2 having a positive refractive power. An aperture stop S is disposed between the first lens unit G1 and the second lens unit G2.

The first lens unit G1 includes a negative meniscus lens L1 having a convex surface directed toward the object side and a positive meniscus lens L2 having a convex surface directed toward the object side.

The second lens unit G2 includes a biconvex positive lens L3, a negative meniscus lens L4 having a convex surface directed toward an image side, and a biconcave negative lens L5. The biconvex positive lens L3, the negative meniscus lens L4, and the biconcave negative lens L5 are cemented.

The aperture stop S is disposed between the positive meniscus lens L2 and the biconvex positive lens L3. A light-receiving surface (image pickup surface) I is a spherical surface, and is curved to be concave toward the object side. The negative meniscus lens L4 is the first lens and the biconcave negative lens L5 is the second lens.

An aspheric surface is provided to five surfaces namely, an image-side surface of the negative meniscus lens L1, an object-side surface of the biconvex positive lens L3, a cemented surface of the biconvex positive lens L3 and the negative meniscus lens L4, a cemented surface of the negative meniscus lens L4 and the biconcave negative lens L5, and an image-side surface of the biconcave negative lens L5.

At the time of zooming from a wide angle end to a telephoto end, the first lens unit G1, after moving toward the image side, moves toward the object side, and the second lens unit G2 moves toward the object side.

Figure 7:
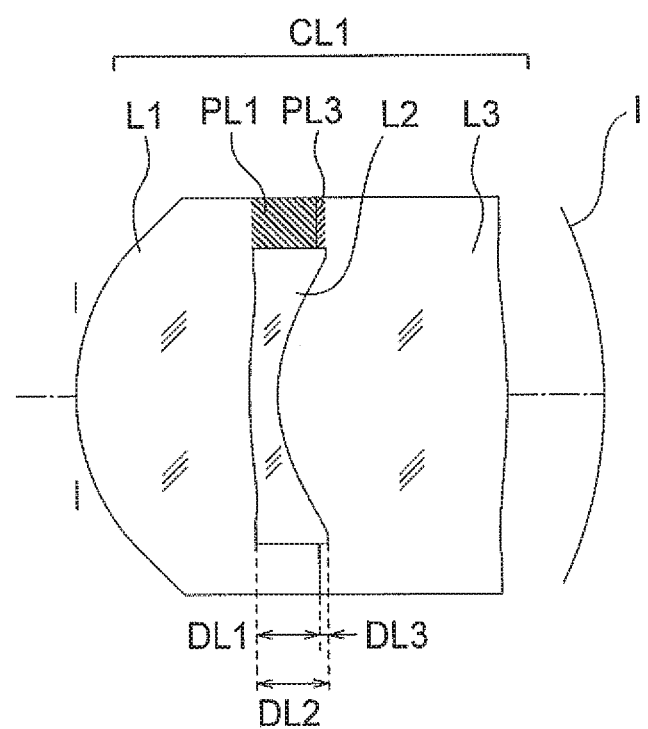
FIG. 7 is a cross-sectional view showing a structure of an image forming optical system.

The image forming optical system according to each example has a cemented lens. A structure of the cemented will be described below. FIG. 7 is a diagram showing a structure of a cemented lens. A cemented lens CL1 includes a lens L1, a lens L2, and a lens L3.

In the lens L1, a projection PL1 is formed on a circumferential portion. In the lens L3, a projection PL3 is formed on a circumferential portion. Both of a length DL1 of the projection PL1 and a length DL3 of the projection PL3 are shorter than a thickness DL2 of the lens L2. In this case, it is possible to fabricate the cemented lens CL1 by cementing.

Each of the lens L1, the lens L2, and the lens L3 is formed by injection molding. Moreover, the three lenses are cemented by applying a cementing material to both surfaces of the lens L2. In such manner, it is possible to fabricate the cemented lens CL1.

Figure 8:
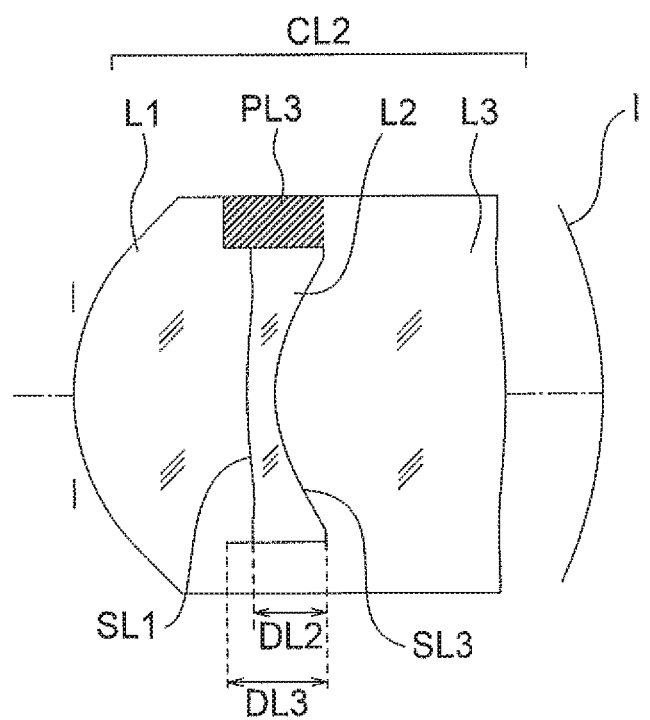
FIG. 8 is a cross-sectional view showing another structure of an image forming optical system.

FIG. 8 is a diagram showing another structure of a cemented lens. A cemented lens CL2 includes a lens L1, a lens L2, and a lens L3.

In the lens L3, a projection PL3 is formed on a circumferential portion. A length DL3 of the projection PL3 is longer than a thickness DL2 of the lens L2. In this case, it is possible to manufacture the cemented lens by curing upon bringing in close contact.

Each of the lens L1 and the lens L3 is manufactured by injection molding. Next, a desired amount of a lens material (such as an energy-curable resin) of the second lens L2 is jetted on to a lens surface SL3. A protrusion PL3 is formed on a lens surface SL3 side. Accordingly, the lens material is held on the lens surface SL3. In this state, the lens L1 is pressed against the lens material. As a result, a lens surface SL1, the lens surface SL3, and the lens material are brought into close contact.

Next, energy is imparted to the lens material. For example, when the lens material is an ultraviolet-cured resin, ultraviolet rays are irradiated on to the lens material. By irradiation of the ultraviolet rays on to the lens material, the lens material is cured to be in a state of making a close contact with the lens surface SL1 and the lens surface SL3. In such manner, it is possible to fabricate the cemented lens CL2.

In curing upon bringing in close contact, the cementing material is not used. However, it is possible to fabricate a cemented lens in the same manner as in a case in which the cementing material is used.

Instead of pressing the lens L1 against the lens material, a mold may be pressed against the lens material. The mold has a surface which is in contact with the lens material. A shape of the contact surface is same as that of a surface of the lens surface SL1. A case of pressing the mold against the lens material will be described below.

Each of the lens L1 and the lens L3 is fabricated by injection molding. Next, a desired amount of a lens material of the lens L2 is jetted on to the lens surface SL3. The lens material is cured in a state of the mold pressed against the lens material. Accordingly, the lens L2 is molded. When the molding of lens L2 is completed, the mold is to be separated from the lens L2. The lens L1 may be cemented to the lens L2 by using a cementing material after molding the lens L2.

The cemented lens CL2 may be fabricated similarly as the cemented lens CL1. In other words, the three lenses may be formed by grinding or by injection molding, and the three lenses may be cemented by using a cementing material.

Figure 9:
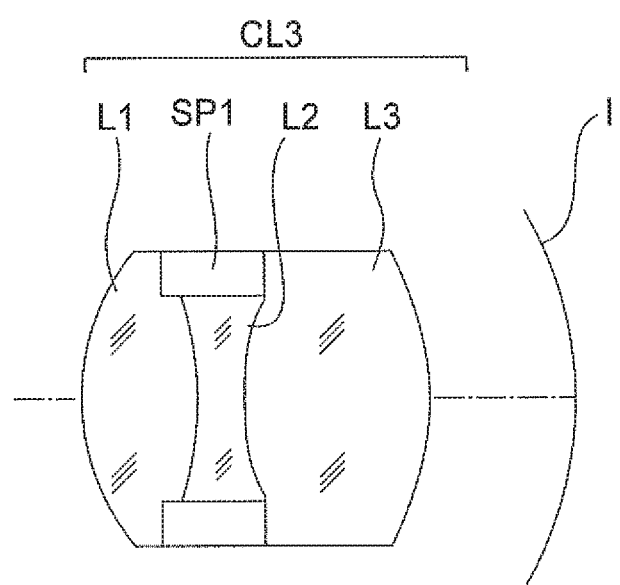
FIG. 9 is a cross-sectional view showing still another structure of an image forming optical system.

FIG. 9 is a diagram showing another structure of a cemented lens. A cemented lens CL3 includes a lens L1, a lens L2, a lens L3, and a frame member SP1. In this case, it is possible to fabricate the cemented lens CL3 by any of cementing and curing upon bringing in close contact.

In a case of fabricating the cemented lens CL3 by cementing, the lens L1, the lens L2, and the lens L3 are fabricated by grinding or injection molding. After fixing the lens L2 to the frame member SP1, a cementing material may be applied to both surfaces of the lens L2, and the three lenses may be cemented.

In a case of fabricating the cemented lens CL3 by curing upon bringing in close contact, the frame member SP1 is fixed to the lens L3. The frame member SP1 has a same function as the projection PL3 shown in FIG. 8. Therefore, it is possible to fabricate the cemented lens CL3 by curing upon bringing in close contact.

Figure 10:
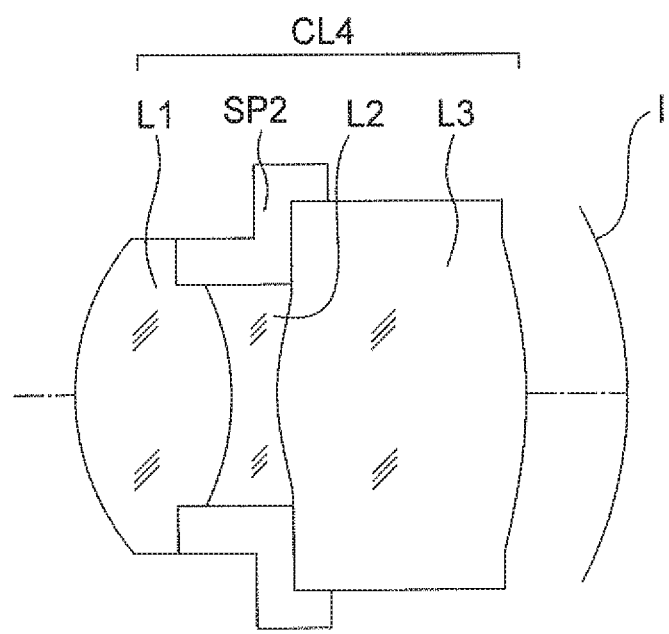
FIG. 10 is a cross-sectional view showing still another structure of an image forming optical system.

FIG. 10 is a diagram showing another structure of a cemented lens. A cemented lens CL4 includes a lens L1, a lens L2, a lens L3, and a frame member SP2. In this case, it is possible to fabricate the cemented lens by any of cementing and curing upon bringing in close contact.

In the cemented lens CL4, the lens L2 and the lens L3 are held by the frame member SP2. Accordingly, it is possible to hold the cemented lens CL4 more stably.

Figure 11:
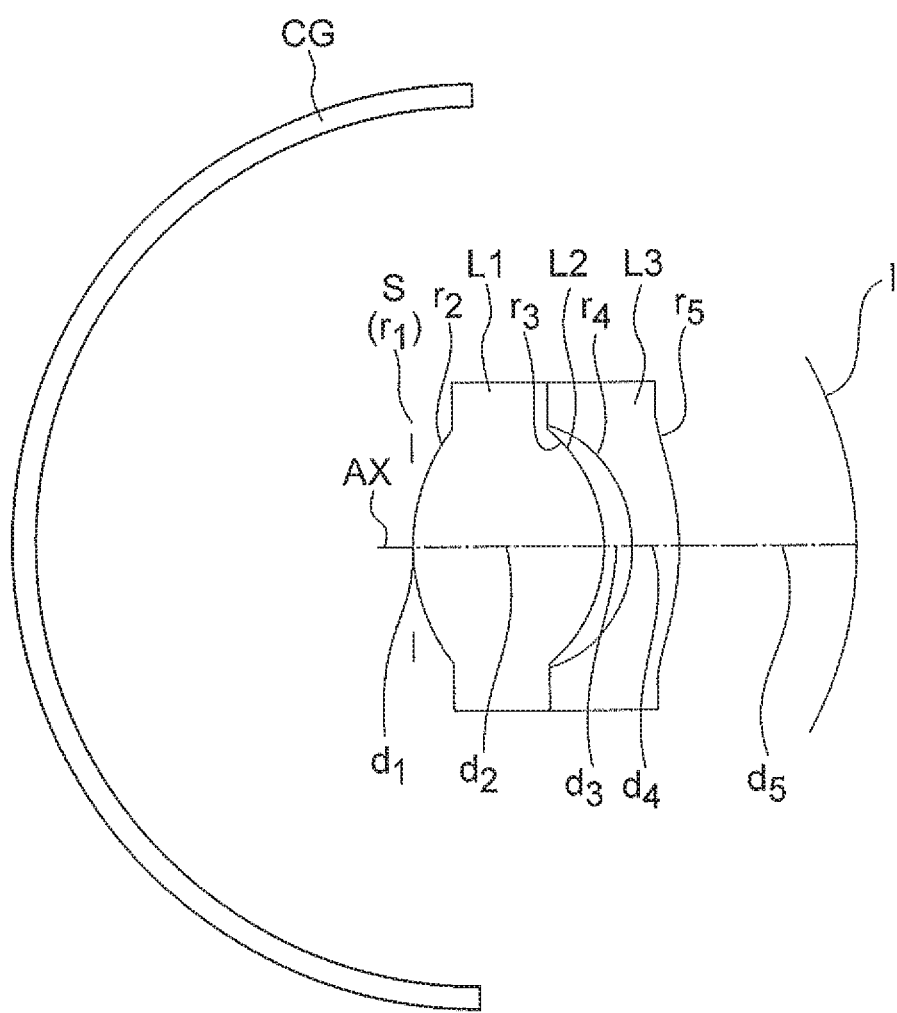
FIG. 11 is a cross-sectional view showing an image pickup apparatus according to an example 6.

An image pickup apparatus according to an example 6, as shown in FIG. 11, includes in order from an object side, an optical member CG, a biconvex positive lens L1, a negative meniscus lens L2 having a convex surface directed toward an image side, and a negative meniscus lens L3 having a convex surface directed toward the image side. A light-receiving surface (an image pickup surface) I is a spherical surface, and is curved to be concave toward the object side. An optical system including the biconvex positive lens L1, the negative meniscus lens L2 and the negative meniscus lens L3 is same as an optical system in the example 1.

FIG. 11 is a schematic diagram exemplifying that the optical member CG can be disposed. Therefore, a size and position of the CG has not been depicted accurately with respect to sizes and positions of lenses.

The optical member CG is a bowl-shaped (dome-shaped) member, and both of an object-side surface and an image-side surface thereof are curved surfaces. In FIG. 11, since both the object-side surface and the image side surface are spherical surfaces having same center of curvature, an overall shape of the optical member is hemispherical. In the present example, a thickness of the optical member CG, or in other words, a distance between the object-side surface and the image side surface is constant in a direction toward the center of curvature.

A material that transmits light is used for the optical member CG. Therefore, light from an object passes through the optical member CG and is incident on the positive lens L1. The optical member CG is disposed such that the center of curvature of the image-side surface substantially coincides with a position of an entrance pupil. Consequently, no new aberration due to the optical member CG occurs practically. In other words, an imaging performance of an image forming optical system in the image pickup apparatus according to the example 6 is same as an imaging performance of an image forming optical system in the image pickup apparatus according to the example 1.

The optical member CG functions as a cover glass. In this case, the optical member CG corresponds to an observation window provided to an outer covering of a capsule endoscope. Therefore, the image pickup apparatus according to the example 6 can be used in an optical system of a capsule endoscope. Image pickup apparatuses according to the examples 2 to 5 can also be used in an optical system of a capsule endoscope.

Numerical data for each of the abovementioned examples is shown below. In surface data, r denotes a radius of curvature of each lens surface, d denotes a distance between two lenses, nd denotes a refractive index about a d-line of each line, υd denotes Abbe's number for each lens, * mark denotes an aspheric surface.

Moreover, in various data, f denotes a focal length of an overall system, FNO denotes an F-number, ω denotes a half angle of view, IH denotes an image height, BF denotes a back focus, and LTL denotes an overall length of an optical system. Here, back focus is a distance from a lens surface nearest to image up to a paraxial image plane indicated upon being subjected to air-conversion. The overall length is a length obtained by adding BF (back focus) to a distance from a lens surface nearest to object up to a lens surface nearest to image of an image forming optical system. Moreover, fL1, fL2, fL3, fL4 and fL5 denote focal lengths of respective lens. Moreover, f1 and f2 denote focal lengths of respective lens units. The unit of the half angle of view is degrees. The focal length of lens and the focal length of lens unit are a focal length for the d-line respectively.

Moreover, when z is let to be an optical axis, y is let to be a direction orthogonal to the optical axis, k is let to be a conical coefficient, and A4, A6, A8, A10, A12, . . . are let to be aspherical-surface coefficients, a shape of the aspheric surface is expressed by the following expression.

$$z=(y^2/r)/[1+\{1-(K+1)(y/r)^2\}^{1/2}]+A4y^4+A5y^6+A8y^8+A10y^{10}+A12y^{12}+\ldots$$

Moreover, 'e-n' (where, n is an integral number) indicates '$10^{-n}$'. Symbols of these original values are same even in the numerical data for the examples that will be described later.

Example 1

| Unit mm | | | | |
|---|---|---|---|---|
| Surface data | | | | |
| Surface no. | r | d | nd | vd |
| Object plane | ∞ | ∞ | | |
| 1 (Stop) | ∞ | 0.00 | | |
| 2* | 1.999 | 2.04 | 1.49700 | 81.54 |
| 3 | −1.630 | 0.30 | 1.63387 | 23.38 |
| 4* | −1.906 | 0.50 | 1.68948 | 31.02 |
| 5* | −3.062 | 1.89 | | |
| Image plane | −4.111 | | | |

Aspherical Surface data

2nd surface k = 0.224
A4 = −7.12218e−03, A6 = −1.83811e−03

4th surface k = −0.743
A4 = −2.63663e−01, A6 = 2.46286e−01, A8 = −1.06551e−01

5th surface k = −1.718
A4 = 5.62017e−03, A6 = 1.95319e−03, A8 = 2.31464e−03

| Various data | |
|---|---|
| f | 3.29 |
| FNO. | 1.81 |
| 2ω | 70.0 |
| LTL | 4.7 |
| BF | 1.89 |
| fL1 | 2.22072 |
| fL2 | −30.7044 |
| fL3 | −8.8993 |

Example 2

| Unit mm | | | | |
|---|---|---|---|---|
| Surface data | | | | |
| Surface no. | r | d | nd | vd |
| Object plane | ∞ | ∞ | | |
| 1 (Stop) | ∞ | 0.00 | | |
| 2* | 2.374 | 1.84 | 1.49700 | 81.54 |
| 3* | 6.850 | 0.30 | 1.63387 | 23.38 |
| 4* | 1.549 | 2.45 | 1.74320 | 49.29 |
| 5* | −7.047 | 1.03 | | |
| Image plane | −4.664 | | | |

Aspherical Surface data

2nd surface k = −1.134
A4 = 8.67770e−03, A6 = −9.92460e−04, A8 = 1.15814e−03

3rd surface k = 2.721
A4 = 1.08845e−02, A6 = −2.12218e−02

4th surface k = −1.754
A4 = −4.11515e−02, A6 = 2.70527e−02, A8 = −7.55573e−03

5th surface k = −43.536
A4 = −4.97411e−04, A6 = 3.08807e−03, A8 = −4.63179e−05

| Various data | |
|---|---|
| f | 3.26 |
| FNO. | 1.81 |
| 2ω | 70.0 |
| LTL | 5.62 |
| BF | 1.03 |
| fL1 | 6.43058 |
| fL2 | −3.22768 |
| fL3 | 1.94473 |

Example 3

Unit mm

Surface data

| Surface no. | r | d | nd | νd |
|---|---|---|---|---|
| Object plane | ∞ | ∞ | | |
| 1 (Stop) | ∞ | 0.00 | | |
| 2* | 2.108 | 1.67 | 1.49700 | 81.54 |
| 3* | −1.372 | 0.05 | | |
| 4 | −1.247 | 0.30 | 1.63387 | 23.38 |
| 5 | −1.147 | 0.50 | 1.68948 | 31.02 |
| 6* | −2.255 | 2.13 | | |
| Image plane | −4.377 | | | |

Aspherical Surface data

2nd surface k = −1.183
A4 = 4.82992e−03, A6 = 7.27948e−03, A8 = −1.01893e−02

3rd surface k = −1.251
A4 = 9.05011e−02, A6 = −6.32413e−02, A8 = −9.77958e−03

4th surface k = −0.174
A4 = 1.50072e−01, A6 = −2.23850e−02, A8 = 3.63989e−03

5th surface k = −5.311
A4 = −1.10811e−01, A6 = 8.05052e−02, A8 = −1.12041e−01

6th surface k = −2.916
A4 = 1.66386e−02, A6 = 3.46597e−03, A8 = 2.78824e−03

Various data

| | |
|---|---|
| f | 3.25 |
| FNO. | 1.80 |
| 2ω | 70.0 |
| LTL | 4.64 |
| BF | 2.13 |
| fL1 | 1.98813 |
| fL2 | 10.4353 |
| fL3 | −4.15413 |

Example 4

Unit mm

Surface data

| Surface no. | r | d | nd | νd |
|---|---|---|---|---|
| Object plane | ∞ | ∞ | | |
| 1 | 3.220 | 1.00 | 1.80610 | 40.92 |
| 2 | 5.456 | 0.51 | | |
| 3 (Stop) | ∞ | 0.00 | | |
| 4* | 4.936 | 1.64 | 1.67790 | 54.89 |
| 5* | −0.664 | 0.30 | 1.63387 | 23.38 |
| 6* | −0.500 | 1.19 | 1.68948 | 31.02 |
| 7* | −2.855 | 1.23 | | |
| Image plane | −4.140 | | | |

Aspherical Surface data

4th surface k = 0.036
A4 = −7.49616e−03, A6 = 2.14495e−03, A8 = −8.90755e−04,
A10 = −4.67383e−04

5th surface k = −1.037
A4 = 8.31945e−02, A6 = 3.84178e−01, A8 = −6.71274e−01,
A10 = 2.58970e−01

6th surface k = −0.963
A4 = 2.67657e−01, A6 = 7.47865e−02, A8 = −3.11120e−01,
A10 = 1.29976e−01

7th surface k = −5.786
A4 = −3.27650e−03, A6 = −1.52645e−03, A8 = 1.15111e−03,
A10 = −1.58715e−04

Various data

| | |
|---|---|
| f | 3.31 |
| FNO. | 1.48 |
| 2ω | 70.0 |
| LTL | 5.87 |
| BF | 1.23 |
| fL1 | 8.07337 |
| fL2 | 0.975402 |
| fL3 | 1.844 |
| fL4 | −1.10164 |

Example 5

Unit mm

Surface data

| Surface no. | r | d | nd | νd |
|---|---|---|---|---|
| Object plane | ∞ | ∞ | | |
| 1 | 280.642 | 1.10 | 1.80625 | 40.91 |
| 2* | 4.524 | 1.42 | | |
| 3 | 7.690 | 3.73 | 2.00069 | 25.46 |
| 4 | 15.841 | Variable | | |
| 5 (Stop) | ∞ | −0.50 | | |
| 6* | 3.744 | 4.00 | 1.49700 | 81.54 |
| 7* | −10.813 | 0.50 | 1.63387 | 23.38 |
| 8* | −12.855 | 4.00 | 1.68948 | 31.02 |
| 9* | 400.588 | Variable | | |
| 10 | ∞ | 0.50 | 1.51633 | 64.14 |
| 11 | ∞ | 1.00 | | |
| Image plane | −65.361 | | | |

Aspherical Surface data

2nd surface k = −1.054
A4 = 6.55457e−04, A6 = 6.58358e−06, A8 = −2.46289e−07,
A10 = 2.78647e−09

6th surface k = −0.046
A4 = −8.80173e−05, A6 = −5.58790e−05, A8 = 1.71697e−05,
A10 = −1.02603e−07

-continued

Unit mm

7th surface k = 25.043
A4 = −1.65043e−02, A6 = 5.74313e−03, A8 = −1.33500e−03,
A10 = 1.03147e−04
8th surface k = −20.000
A4 = 2.70164e−04, A6 = −1.54152e−02, A8 = 2.73175e−03,
A10 = −1.67175e−04
9th surface k = 0.000
A4 = 4.26655e−04, A6 = −1.52933e−04, A8 = 3.30331e−05,
A10 = −1.04529e−06

Zoom data

|  | WE | ST | TE |
|---|---|---|---|
| f | 5.00 | 10.01 | 14.81 |
| FNO. | 3.31 | 4.45 | 5.54 |
| 2ω | 82.84 | 42.65 | 28.86 |
| IH | 3.80 | 3.80 | 3.80 |
| LTL | 33.95 | 28.92 | 29.74 |
| BF | 6.46 | 10.29 | 13.98 |
| d4 | 13.24 | 4.39 | 1.51 |
| d9 | 5.11 | 8.95 | 12.74 |

Various data

| fL1 | −5.71268 |
|---|---|
| fL2 | 12.1556 |
| fL3 | 6.15758 |
| fL4 | −118.626 |
| fL5 | −17.9944 |

Unit focal length

| f1 = −10.75 | f2 = 8.24 |
|---|---|

Next, values of the conditional expressions of each of the examples are shown below.

(1) $\beta_{LA}$
(2) $\upsilon d_{LA}$
(3) $|f/R_{img}|$
(4) $\beta hg_{LA}$
(5) $|(Y_e/R_e)-(Y_{img}/R_{img})|$
(6) $|R_1/R_e|$
(7) $L_{1e}/TL$
(8) $PS \times f$
(9) $PS \times EXP$
(10) $\beta_{LB}$
(11) $\beta hg_{LB}$

|  | Example 1 | Example 2 | Example 3 | Example 4 | Example 5 |
|---|---|---|---|---|---|
| (1) | 0.71 | 0.71 | 0.71 | 0.71 | 0.71 |
| (2) | 23.38 | 23.38 | 23.38 | 23.38 | 23.38 |
| (3) | 0.80 | 0.70 | 0.74 | 0.80 | 0.08 |
| (4) | 0.67 | 0.67 | 0.67 | 0.67 | 0.67 |
| (5) | 0.12 | 0.20 | 0.02 | 0.01 | 0.06 |
| (6) | 0.65 | 0.34 | 0.94 | 1.13 | 0.70 |
| (7) | 0.60 | 0.82 | 0.54 | 0.79 | 0.81 |
| (8) | 0.84 | 0.76 | 0.82 | 0.88 | 0.09 |
| (9) | −1.15 | −1.27 | −1.14 | −1.16 | −0.19 |
| (10) | 0.65 | 0.63 | 0.65 | 0.65 | 0.65 |
| (11) | 0.60 | 0.57 | 0.60 | 0.60 | 0.60 |

Moreover, values of a relative partial dispersion of each of the examples are shown below.

|  | Example 1 | Example 2 | Example 3 | Example 4 | Example 5 |
|---|---|---|---|---|---|
| $\theta g F_{LA}$ | 0.668 | 0.668 | 0.668 | 0.668 | 0.668 |
| $\theta g F_{LB}$ | 0.5987 | 0.5529 | 0.5987 | 0.5987 | 0.5987 |
| $\theta h g_{LA}$ | 0.622 | 0.622 | 0.622 | 0.622 | 0.622 |
| $\theta h g_{LB}$ | 0.5304 | 0.4632 | 0.5304 | 0.5304 | 0.5304 |

FIG. 12 illustrates a schematic arrangement of a capsule endoscope according to an example. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, an illuminating portion 104, an image pickup element 105, a drive control unit 106, and a signal processing unit 107. The transparent cover 102 is disposed at a position where both a font surface of the image forming optical system 103 and a font surface of the illuminating portion 104 are covered at the same time. Although it is not shown in the diagram, the interior of the capsule endoscope 100 is provided with an electric-power receiving unit and a transmitting unit.

Illumination light is irradiated from the illuminating portion 104. The illumination light passes through the transparent cover 102 and is irradiated to an object. Light from the object is incident on the image forming optical system 103. An optical image of the object is formed at an image position by the image forming optical system 103.

The optical image is picked up by the image pickup element 105. A drive and control of the image pickup element 105 is carried out by the drive control unit 106. Moreover, an output signal from the image pickup element 105 is processed by the signal processing unit 107 according to the requirement.

Here, for the image forming optical system 103, an optical system which includes the image pickup apparatus according to the abovementioned example 1 has been used. Therefore, an optical image with a favorable optical performance is formed. Moreover, the optical image is curved to be concave toward the object side.

A light-receiving surface (an image pickup surface) of the image pickup element 105 is curved to be concave toward the object side. Moreover, a radius of curvature of the light-receiving surface (image pickup surface) is same as a radius of curvature of the optical image. Consequently, it is possible to achieve an image which is sharp from a center up to periphery, while being an image captured with a favorable optical performance.

Figure 13A:
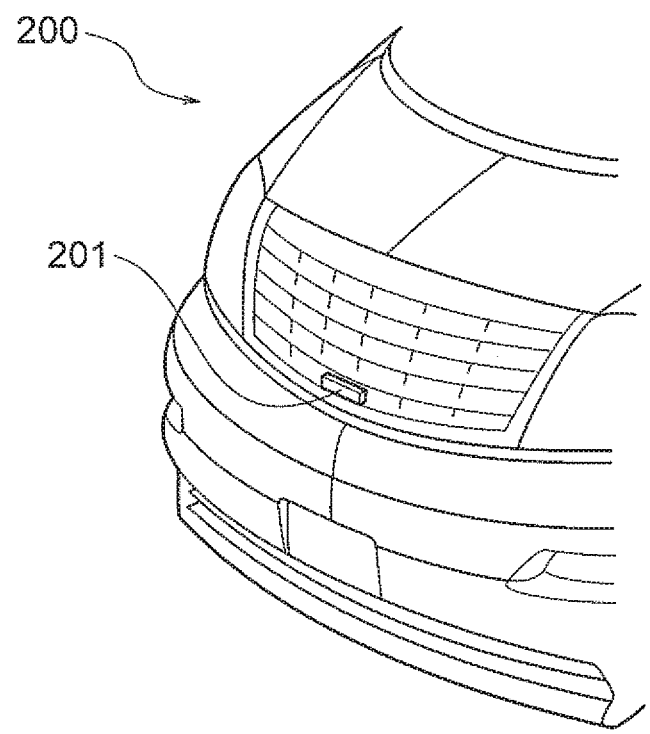
FIG. 13A and FIG. 13B are diagrams showing a car-mounted camera where.
Figure 13B:
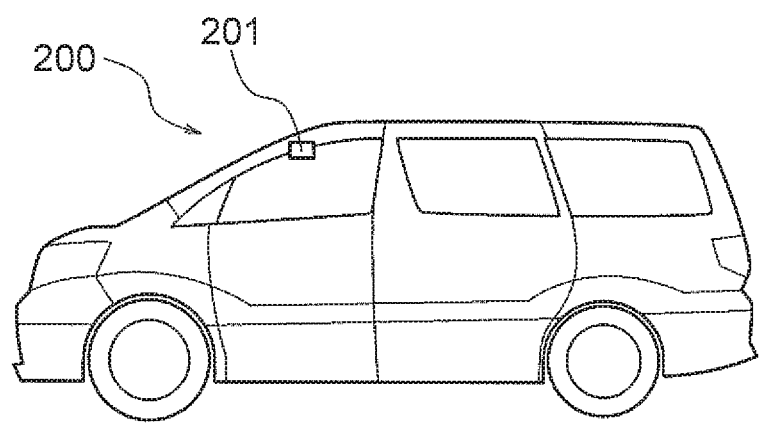

FIG. 13A and FIG. 13B are examples of another image pickup apparatus. This is an example of a car-mounted camera. FIG. 13A is a diagram showing an example of a car-mounted camera mounted at an outside of a car, and FIG. 13B is a diagram showing an example of a car-mounted camera mounted inside the car.

As shown in FIG. 13A, a car-mounted camera 201 is provided to a front grill of a car 200. The car-mounted camera 201 includes an image forming optical system and an image pickup element.

For the image forming optical system of the car-mounted camera 201, the optical system that includes the image pickup apparatus according to the abovementioned example 1 is used. Therefore, an optical image of a wide range is formed. Moreover, a light-receiving surface (an image pickup surface) of the image pickup element is curved to be concave toward the object side. Furthermore, a radius of curvature of the light-receiving surface (image pickup surface) is same as a radius of curvature of the optical image. Consequently, it is possible to achieve an image which is sharp from a center up to a periphery, while being an image captured over an extremely wide range.

As shown in FIG. 13B, the car-mounted camera 201 is provided near a ceiling of the car 200. An action and effect of the car-mounted camera 201 is as already described.

The car-mounted camera 201, when to be provided outside, may be disposed at each corner and at the top of a pole of a head portion. Moreover, the car-mounted camera 201, when to be provided inside, may be provided near a back mirror.

Moreover, it is preferable to satisfy the plurality of abovementioned inventions simultaneously as each of the effects of small-sizing, high performance, and widening of angle of view is more assured.

Various embodiments of the present invention have been described heretofore. However, the present invention is not limited only to these embodiments, and embodiments in which arrangements of these embodiments have been combined appropriately without departing from the scope of the invention are also within the scope of the present invention.

The present invention shows an effect that it is possible to provide an image pickup apparatus having an image forming optical system in which a chromatic aberration in a wide wavelength region is corrected favorably, and a capsule endoscope.

In such manner, the present invention is useful for an image pickup apparatus in which the Petzval's sum for the optical system is not required to be made small and it is easy to reduce the number of lenses and carry out small-sizing, and which is advantageous for the correction of chromatic aberration and enables to achieve a favorable optical performance, and for a capsule endoscope.

What is claimed is:

1. An image pickup apparatus comprising:
an image forming optical system which includes an aperture stop that sets an axial light beam, a first lens, and a second lens; and
an imager which is disposed on an image side of the image forming optical system, and has a light-receiving surface which is not flat and is curved to be concave toward the image forming optical system,
wherein:
a relative partial dispersion for a medium of the first lens differs from a relative partial dispersion for a medium of the second lens,
in a first rectangular coordinate system in which a horizontal axis is $vd_{LA}$ and a vertical axis is $\theta gF_{LA}$, when a straight line indicated by $\theta gF_{LA}=\alpha \times vd_{LA}+\beta_{LA}$ (where $\alpha=-0.00163$) has been set, $\theta gF_{LA}$ and $vd_{LA}$ for the medium of the first lens are included in both of an area in the first rectangular coordinate system determined by the following conditional expression (1) and an area in the first rectangular coordinate system determined by the following conditional expression (2), and the following conditional expression (3) is satisfied:

$$0.68 < \beta_{LA} \quad (1)$$

$$vd_{LA} < 50 \quad (2), \text{ and}$$

$$0 < |f/R_{img}| \le 1.5 \quad (3)$$

where,
$\theta gF_{LA}$ denotes the relative partial dispersion $(ng_{LA}-nF_{LA})/(nF_{LA}-nC_{LA})$ for the medium of the first lens,
$vd_{LA}$ denotes Abbe number $(nd_{LA}-1)/(nF_{LA}-nC_{LA})$ for the medium of the first lens,
$nd_{LA}$, $nC_{LA}$, $nF_{LA}$, and $ng_{LA}$ denote refractive indices of the medium of the first lens for a d-line, a C-line, an F-line, and a g-line respectively,
$R_{img}$ denotes a radius of curvature of a virtual spherical surface including a surface apex and a point at which a principal light ray with the maximum image height of the image forming optical system and the light-receiving surface intersect, when a point of intersection of an optical axis of the image forming optical system and the light-receiving surface is the surface apex,
f denotes a focal length of the image forming optical system for the d-line, and
when the focal length of the image forming optical system is variable, conditional expression (3) is a conditional expression in a state at a wide angle end.

2. The image pickup apparatus according to claim 1, wherein in a second rectangular coordinate system in which a horizontal axis is $vd_{LA}$ and a vertical axis is $\theta hg_{LA}$, when a straight line indicated by $\theta hg_{LA}=\alpha hg \times vd_{LA}+\beta hg_{LA}$ (where $\alpha hg=-0.00225$) has been set, $\theta hg_{LA}$ and $vd_{LA}$ for the medium of the first lens are included in both of an area in the second rectangular coordinate system determined by the following conditional expression (4) and an area in the second rectangular coordinate system determined by the following conditional expression (2):

$$0.65 < \beta hg_{LA} \quad (4), \text{ and}$$

$$vd_{LA} < 50 \quad (2)$$

where,
$\theta hg_{LA}$ denotes a relative partial dispersion $(nh_{LA}-ng_{LA})/(nF_{LA}-nC_{LA})$ for the medium of the first lens, and
$nh_{LA}$ denotes a refractive index for an h-line of the medium of the first lens.

3. The image pickup apparatus according to claim 1, wherein the first lens and the second lens are cemented.

4. The image pickup apparatus according to claim 3, wherein:
the first lens is a resin lens, and
the first lens is cured upon being brought in close contact with a refracting surface of the second lens.

5. The image pickup apparatus according to claim 1, wherein a sign of a focal length of the first lens differs from a sign of a focal length of the second lens.

6. The image pickup apparatus according to claim 1, wherein the first lens has at least one aspheric surface.

7. The image pickup apparatus according to claim 6, wherein the aspheric surface of the first lens is an aspheric surface for which an absolute value of a curvature becomes smaller gradually toward a direction of separating away from the optical axis.

8. The image pickup apparatus according to claim 6, wherein the aspheric surface of the first lens is an aspheric surface having a point of inflection in an effective area on a cross-sectional surface including an axial principal light ray.

9. The image pickup apparatus according to claim 1, wherein the aperture stop is disposed on an object side of the first lens.

10. The image pickup apparatus according to claim 1, wherein from among lens surfaces in the image forming optical system, a lens surface positioned nearest to image is a surface which is convex toward the image side.

11. The image pickup apparatus according to claim 1, wherein the following conditional expression (5) is satisfied:

$$0 \leq |(Y_e/R_e)-(Y_{img}/R_{img})| < 0.3 \quad (5)$$

where,
$Y_e$ denotes a distance of a point at which a principal light ray at the maximum angle of view of the image forming optical system intersects a surface nearest to image of the image forming optical system from the optical axis,
$R_e$ denotes a paraxial radius of curvature of a surface nearest to image out of lens surfaces in the image forming optical system,
$Y_{img}$ denotes a distance of a point at which the principal light ray at the maximum angle of view of the image forming optical system intersects the light-receiving surface from the optical axis, and
when the focal length of the image forming optical system is variable, conditional expression (5) is a conditional expression in the state at the wide angle end.

12. The image pickup apparatus according to claim 1, wherein the following conditional expression (6) is satisfied:

$$0.5 < |R_1/R_e| \leq 1.5 \quad (6)$$

where,
$R_1$ denotes a paraxial radius of curvature of a surface nearest to object out of lens surfaces of the image forming optical system, and
$R_e$ denotes a paraxial radius of curvature of a surface nearest to image out of the lens surfaces of the image forming optical system.

13. The image pickup apparatus according to claim 1, wherein the following conditional expression (7) is satisfied:

$$0.5 < L_{1e}/TL \quad (7)$$

where,
$L_{1e}$ denotes an actual distance from a lens surface nearest to object on the optical axis up to a predetermined surface different from a cover glass, the predetermined surface being a surface positioned nearest to the light-receiving surface and adjacent to air, from among lens surfaces in the image forming optical system,
TL denotes an actual distance on the optical axis from the lens surface nearest to object up to the light-receiving surface, and
when the focal length of the image forming optical system is variable, conditional expression (7) is a conditional expression in the state at the wide angle end.

14. The image pickup apparatus according to claim 1, wherein the following conditional expression (8) is satisfied:

$$0 < PS \times f < 1 \quad (8)$$

where,
PS denotes Petzval's sum for the image forming optical system, and
Petzval's sum PS is expressed by the following expression:

$$PS = \sum_{i=1}^{k} \frac{1}{n_i \times f_i}$$

where
i denotes an order of lenses from an object side in the image forming optical system,
k denotes a total number of lenses in the image forming optical system,
$n_i$ denotes a refractive index of an $i^{th}$ lens for the d-line,
$f_i$ denotes a focal length of the $i^{th}$ lens for the d-line, and
when the focal length of the image forming optical system is variable, conditional expression (8) is a conditional expression in the state at the wide angle end.

15. The image pickup apparatus according to claim 1, wherein the following conditional expression (9) is satisfied:

$$PS \times EXP < 0 \quad (9)$$

where,
PS denotes Petzval's sum for the image forming optical system, and
Petzval's sum PS is expressed by the following expression:

$$PS = \sum_{i=1}^{k} \frac{1}{n_i \times f_i}$$

where
i denotes an order of lenses from an object side in the image forming optical system,
k denotes a total number of lenses in the image forming optical system,
$n_i$ denotes a refractive index of an $i^{th}$ lens for the d-line,
$f_i$ denotes a focal length of the $i^{th}$ lens for the d-line,
EXP denotes a distance along the optical axis from the light-receiving surface up to a paraxial exit pupil position, and has a negative sign when the paraxial exit pupil position is on an object side of the light-receiving surface, and
when the focal length of the image forming optical system is variable, conditional expression (9) is a conditional expression in the state at the wide angle end.

16. The image pickup apparatus according to claim 1, wherein in a second rectangular coordinate system in which a horizontal axis is $vd_{LB}$ and a vertical axis is $\theta gF_{LB}$, when a straight line indicated by $\theta gF_{LB} = \alpha \times vd_{LB} + \beta_{LB}$ (where $\alpha = -0.00163$) has been set, $\theta gF_{LB}$ and $vd_{LB}$ for the medium of the second lens are included in an area in the second rectangular coordinate system determined by the following conditional expression (10):

$$\beta_{LB} < 0.67 \quad (10)$$

where,
$\theta gF_{LB}$ denotes a relative partial dispersion $(ng_{LB} - nF_{LB})/(nF_{LB} - nC_{LB})$ for the medium of the second lens,
$vd_{LB}$ denotes Abbe number $(nd_{LB} - 1)/(nF_{LB} - nC_{LB})$ for the medium of the second lens, and
$nd_{LB}$, $nC_{LB}$, $nF_{LB}$, and $ng_{LB}$ denote refractive indices of the medium of the second lens for the d-line, the C-line, the F-line, and the g-line respectively.

17. The image pickup apparatus according to claim 1, wherein in a second rectangular coordinate system in which a horizontal axis is $vd_{LB}$ and a vertical axis is $\theta hg_{LB}$, when a straight line indicated by $\theta hg_{LB} = \alpha hg \times vd_{LB} + \beta hg_{LB}$ (where αhg=−0.00225) has been set, $\theta hg_{LB}$ and $vd_{LB}$ for the medium of the second lens are included in an area in the second rectangular coordinate system determined by the following conditional expression (11):

$$\beta hg_{LB} < 0.64 \quad (11)$$

where, $\theta hg_{LB}$ denotes a relative partial dispersion $(nh_{LB}-ng_{LB})/(nF_{LB}-nC_{LB})$ for the medium of the second lens, and $nh_{LB}$ denotes a refractive index for an h-line of the medium of the second lens.

18. The image pickup apparatus according to claim 1, further comprising:
an illuminating portion; and
a cover portion disposed on an object side of the image forming optical system.

19. The image pickup apparatus according to claim 18, wherein the cover portion has a dome shape and covers both the object side of the image forming optical system and an object side of the illuminating portion.

20. A capsule endoscope comprising the image pickup apparatus according to claim 19.

* * * * *